United States Patent [19]

Hutchison et al.

[11] Patent Number: 4,564,018

[45] Date of Patent: Jan. 14, 1986

[54] ULTRASONIC SYSTEM FOR OBTAINING OCULAR MEASUREMENTS

[75] Inventors: Stephen Hutchison, Kirkwood; J. Alan Ritter, Des Peres; Mark Virkus, Ellisville, all of Mo.

[73] Assignee: Storz Instrument Company, St. Louis, Mo.

[21] Appl. No.: 437,487

[22] Filed: Oct. 28, 1982

[51] Int. Cl.[4] .............................................. A61B 10/00
[52] U.S. Cl. ...................................... 128/660; 73/631
[58] Field of Search ........... 128/660; 73/631, 610–617

[56] References Cited

U.S. PATENT DOCUMENTS 4,154,114  5/1979  Katz et al. ....................... 128/660 X
4,261,367  4/1981  Freese ................................ 128/660

OTHER PUBLICATIONS

Storz Corneo-Scan Ultrasonic Pachymeter, Storz Instrument Company, 1982 Model CS1000.
Storz Compu-Scan Biometric Ruler, Storz Instrument Company, revised 5/82 Model U2020.
Kremer, F. B. et al., "Apparatus and Method for Performing Corneal Surgery," International Publ. No. WO82/02485, publ. Aug. 5, 1982.

Primary Examiner—Kyle L. Howell
Assistant Examiner—Francis J. Jaworski
Attorney, Agent, or Firm—Harness, Dickey & Pierce

[57] ABSTRACT

An ultrasonic diagnostic scanner for obtaining ocular measurements is described. The ultrasonic diagnostic scanner generally comprises transmitter means for generating an ultrasonic signal, receiver means for receiving echo signals and for producing a peak signal at substantially the maximum amplitude of the echo signals when the echo signals exceed a predeterminable threshold level, programmable means for producing count signals indicative of the times between the transmission of the ultrasonic signal and the occurrence of a selected number of peak signals, and between the occurrence of predetermined peak signals, microcomputer means for controlling the transmitter and programmable means, and output means for generating a perceptible output indicative of the ocular parameter being measured. The ultrasonic diagnostic scanner also includes sensitivity adjustment means for maintaining a predetermined amplitude level of at least one of the echo signals under the control of the microcomputer means. Threshold adjustment means is also provided for adjusting the predeterminable threshold level under the control of the microcomputer means. A dot matrix liquid crystal display is also included for visually displaying an echo histogram of the echo signals.

24 Claims, 19 Drawing Figures

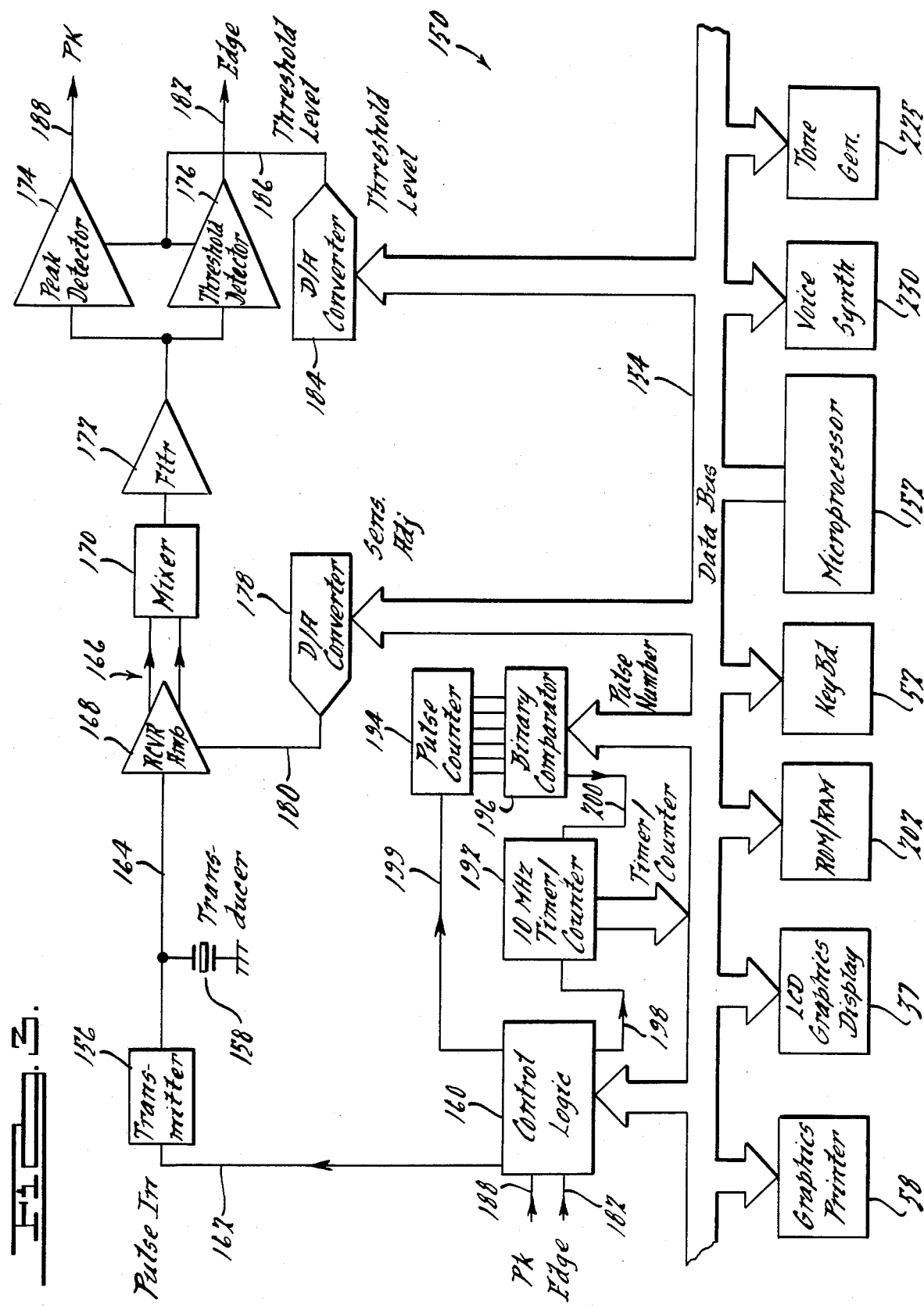

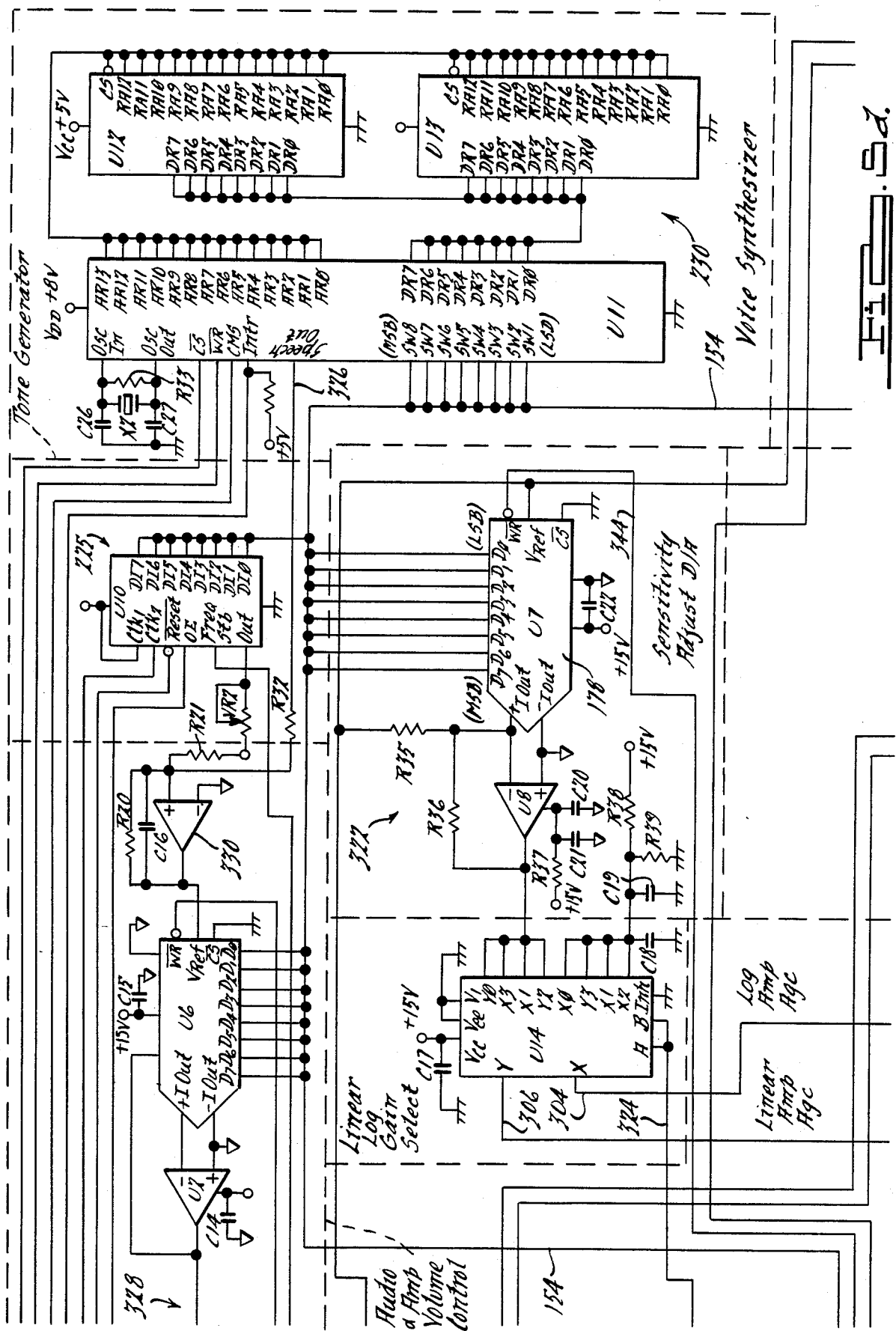

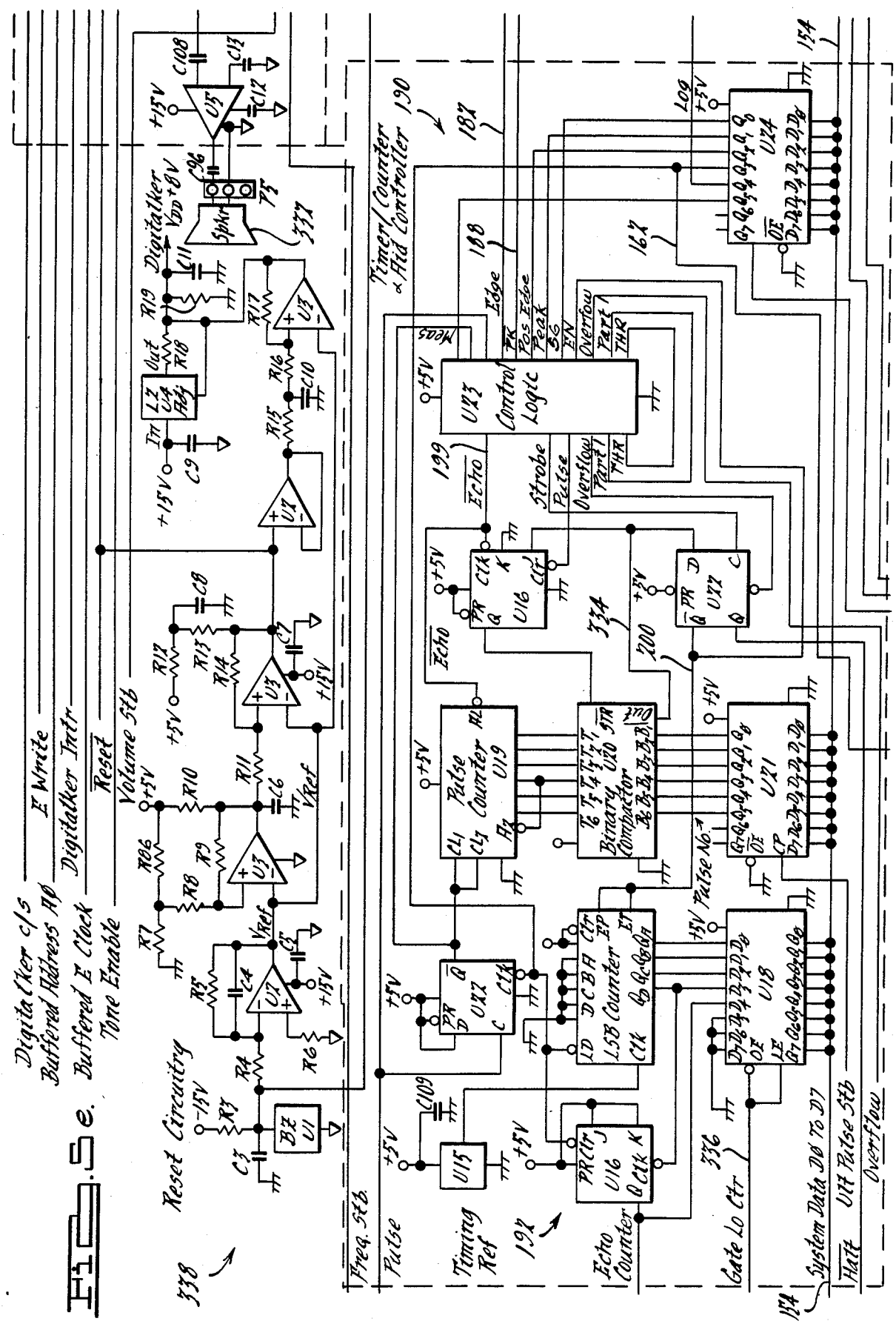

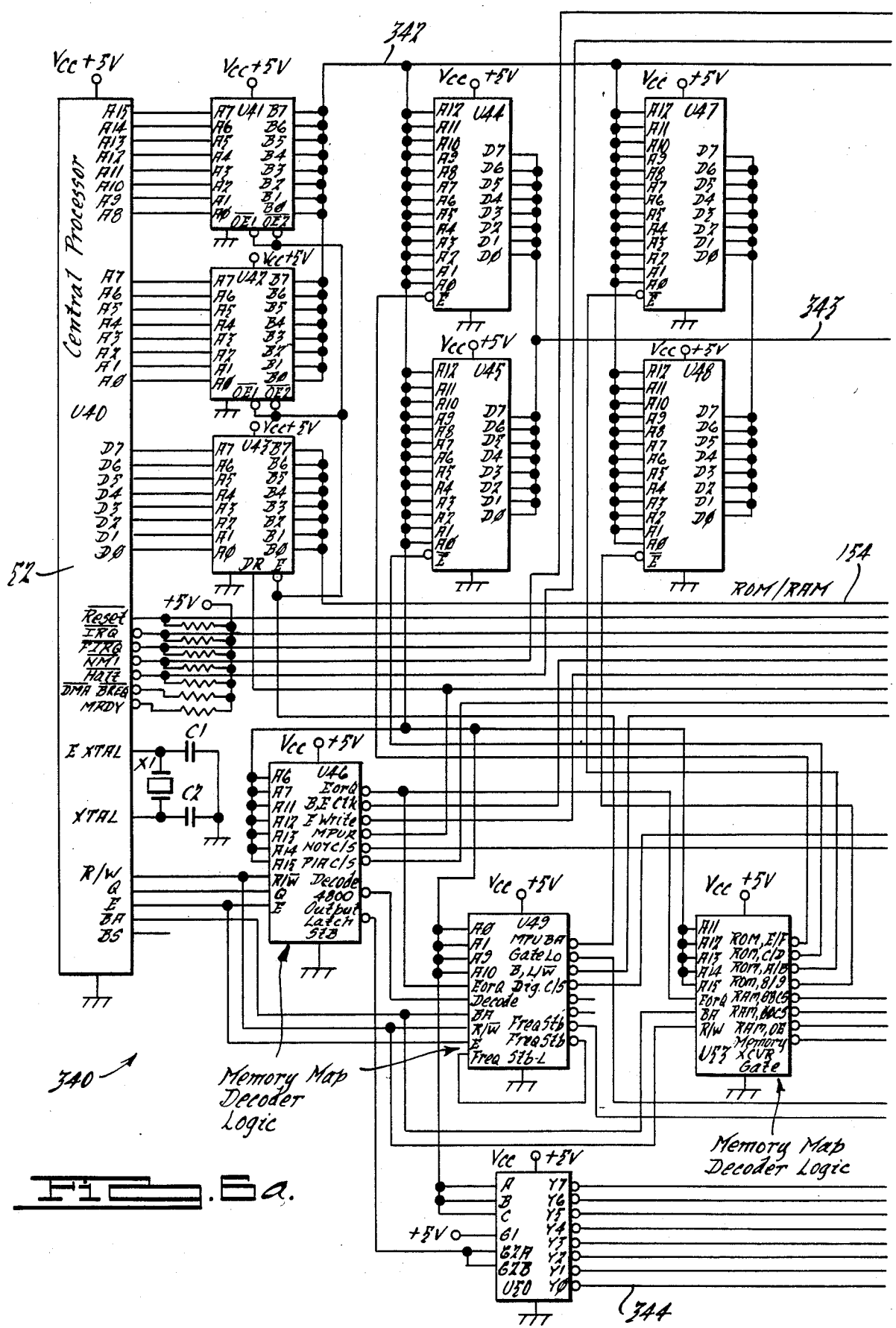

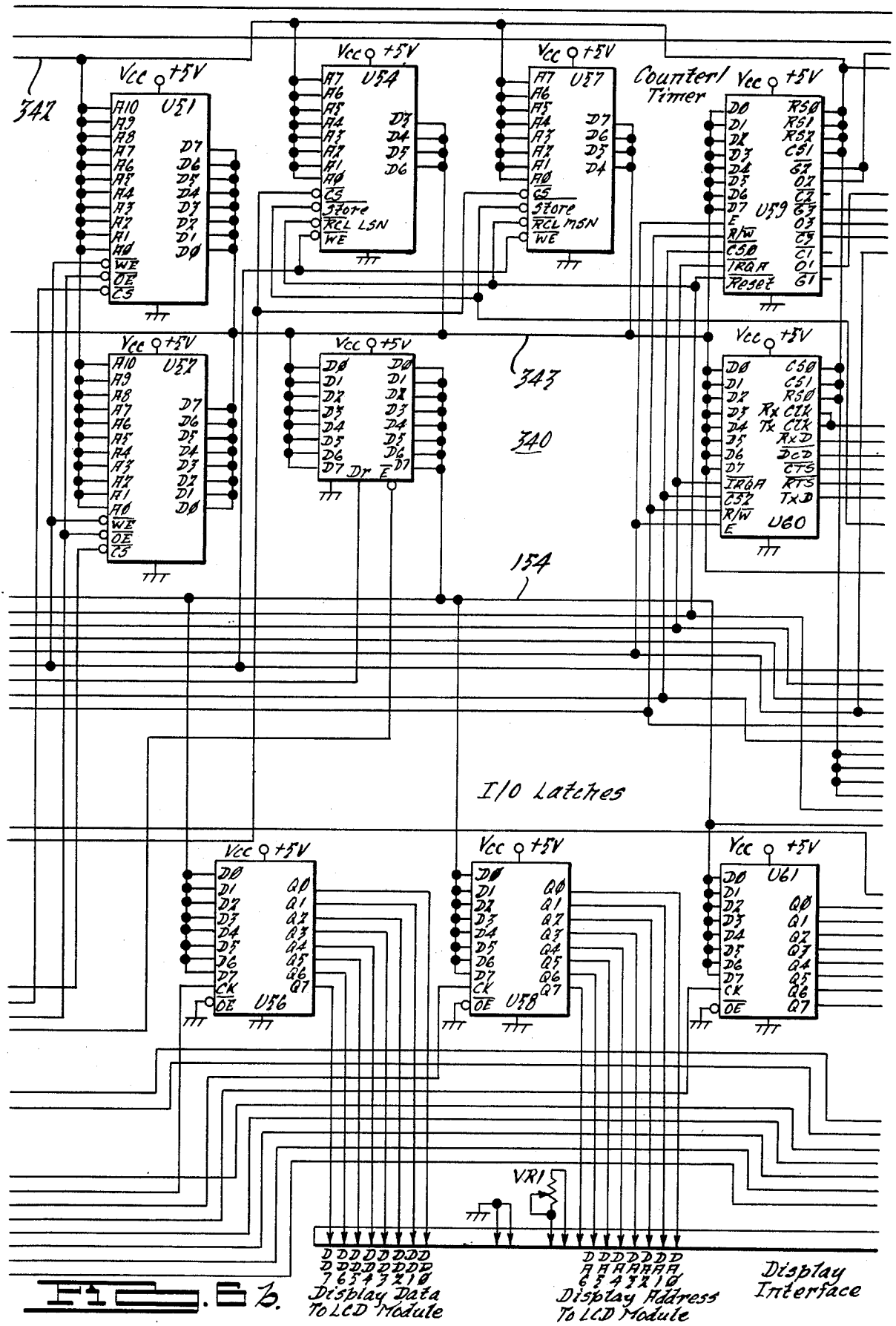

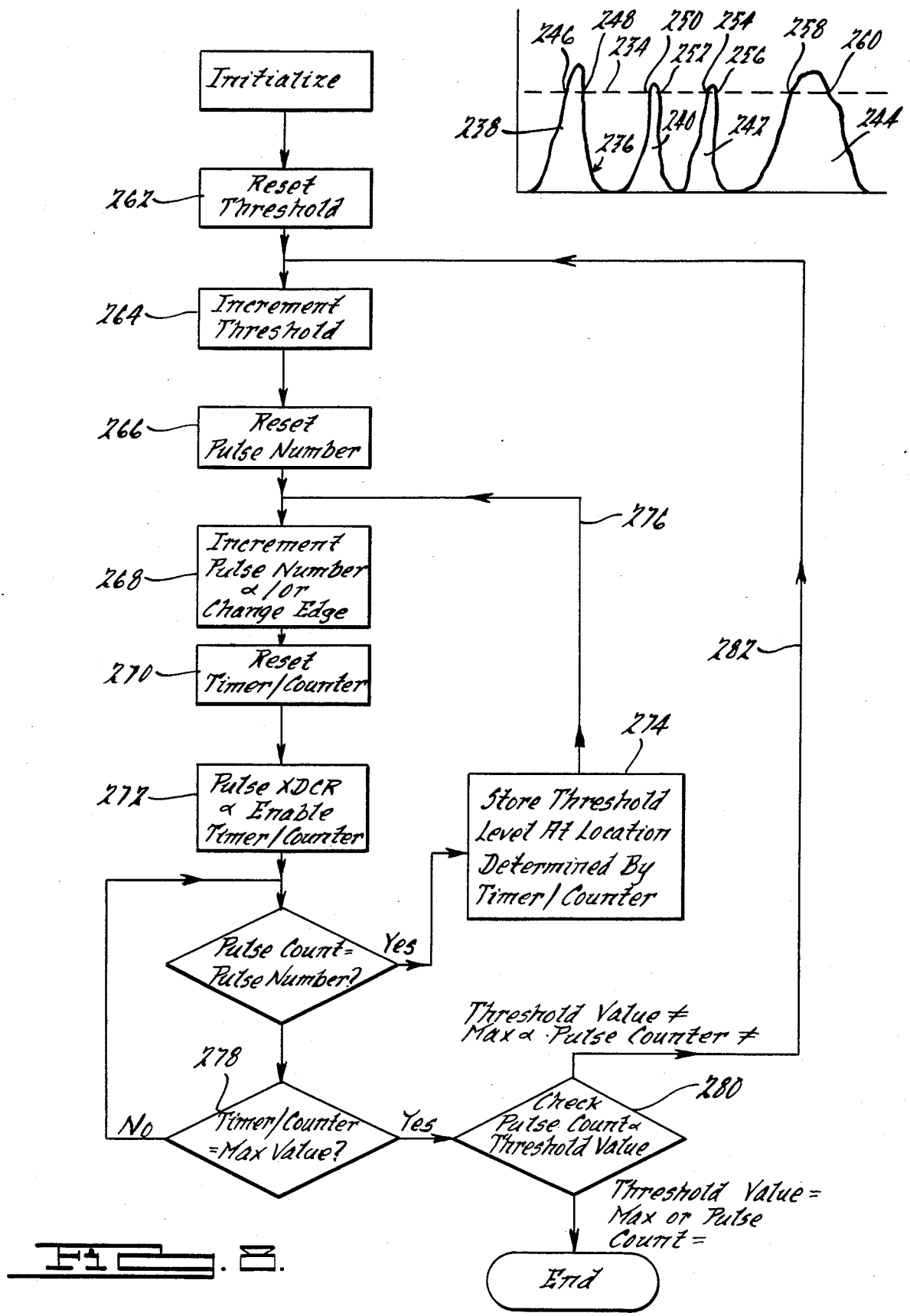

ULTRASONIC SYSTEM FOR OBTAINING OCULAR MEASUREMENTS

BACKGROUND AND SUMMARY OF THE INVENTION

The present invention relates generally to systems for obtaining ocular measurements, and particularly to an ultrasonic diagnostic scanner for measuring the axial length of an eye.

Ultrasonic vibrations or sound waves are frequently used in the field of medicine, for example, to determine information about certain internal characteristics of a person, organ or object. The ultrasonic vibrations are typically transmitted through a probe-type device which is placed in contact with a patient's body or other object, and the vibrations reflected back from internal components or organs are received by the probe. One such application involves ultrasonic diagnostic scanners for measuring the axial length of an eye from the cornea to the retina of the eye. These ultrasonic diagnostic scanners have typically measured the axial length of an eye by examining echo reflections which exceed a certain threshold level and recording or storing the time it takes for a certain number of these echo reflections to occur. This time value may then be related to a distance of length value through well known equations which correlate the time elapsed and the velocity at which the ultrasonic vibration was transmitted.

One or more of these distance equations are usually programmed into the ultrasonic diagnostic scanner so that the axial length measured may be conveniently displayed as a numerical value for the physician conducting the ocular examination. Some prior ultrasonic diagnostic scanners have also employed cathode ray tube video screens so that a real-time image of the echo reflections may be displayed. These ultrasonic diagnostic scanners have generally been classified as "A-Scans" which register only the amplitude of the echo reflections as they return, and "B-Scans" which provide for the brightness modulation or grey-scale variations necessary to produce a two-dimensional image of the eye from the echo reflections.

One example of a prior ultrasonic diagnostic scanner is the COMPU-SCAN (Trademark) Biometric Ruler, model U2020, manufactured by the Storz Instrument Company, the assignee of the present invention. This instrument includes a self-contained computer which performs the necessary lens calculations, and a cathode-ray tube for displaying an A-Scan of the echo reflections. An ultrasonic probe which is useful both for this instrument, as well as for the present invention is disclosed in U.S. patent application Ser. No. 436,845, Filed on Oct. 26, 1982, and entitled "Ultrasonic Probe", now abandoned. This patent application is also assigned to the assignee of the present invention, and is hereby incorporated by reference.

Another instrument useful in obtaining ocular measurements is the CORNEO-SCAN (Trademark) Ultrasonic Pachymeter, model CS1000, also manufactured by the Storz Instrument Company. This instrument is used to measure the thickness of the cornea of an eye, and includes a self-contained computer which performs the corneal thickness calculations, and a liquid crystal display (LCD) for displaying the numerical value of the corneal thickness. This instrument also includes circuitry for producing electronically synthesized speech, such as the word "ready" when the instrument is ready to make a measurement. The speech circuitry in this unit is also capable of reciting the standard deviation value for a number of measurements taken.

It is a principal objection of the present invention to provide an improved ultrasonic system for obtaining ocular measurements.

It is a more specific object of the present invention to provide an improved ultrasonic diagnostic scanner for measuring the axial length of an eye.

It is another object of the present invention to provide an ultrasonic diagnostic scanner capable of detecting an axial misalignment condition.

It is an additional object of the present invention to provide an ultrasonic diagnostic scanner capable of detecting a corneal depression condition.

It is a further object of the present invention to provide an ultrasonic diagnostic scanner capable of automatically adjusting its sensitivity.

It is yet another object of the present invention to provide an ultrasonic diagnostic scanner capable of automatically adjusting the threshold at which echo reflections are processed.

It is yet a further object of the present invention to provide an ultrasonic diagnostic scanner capable of displaying an echo histogram of the echo reflections on a liquid crystal display.

In accordance with the foregoing objects, the present invention provides an ultrasonic diagnostic scanner which generally comprises transmitter means for causing a transducer to transmit an ultrasonic signal, receiver means for receiving echo signals and for producing a peak signal at substantially the maximum amplitude of the echo signals when the echo signals exceed a predeterminable threshold level, programmable means for producing count signals indicative of the times between the transmission of the ultrasonic signal and the occurrence of a selected number of peak signals and between the occurrence of predetermined peak signals, microcomputer means for controlling the transmitter and programmable means, and output means for generating a perceptible output indicative of the ocular parameter being measured. The ultrasonic diagnostic scanner also includes sensitivity adjustment means for maintaining a predetermined amplitude level of at least one of the echo signals under the control of the microcomputer means. Threshold adjustment means is also provided for adjusting the predeterminable threshold level under the control of the microcomputer means. A dot matrix liquid crystal display is also included for visually displaying an echo histogram of the echo signals.

Additional advantages and features of the present invention will become apparent from a reading of the detailed description of the preferred embodiment which makes reference to the following set of drawings in which:

BRIEF DESCRIPTION OF THE DRAWINGS

FIG. 3 is a block diagram of the ultrasonic system circuitry according to the present invention.

FIG. 5d is a schematic diagram of the sensitivity adjustment means according to the present invention, as well as the voice synthesizer and the tone generator shown in FIG. 3.

FIG. 5e is a schematic diagram of the programmable means according to the present invention.

FIGS. 6a–c are schematic diagrams of the microcomputer means according to the present invention.

FIG. 8 is a flow chart of the method used to display an echo histogram in accordance with the present invention.

FIG. 9 is an exploded longitudinal side view of the ultrasonic probe shown in FIG. 1.

FIG. 10 illustrates a gauging device for properly installing the factual membrane on the ultrasonic probe of FIG. 9.

FIG. 11 is a longitudinal side view of a fully assembled ultrasonic probe according to the present invention which employs an alternative membrane retention apparatus.

DETAILED DESCRIPTION OF THE PREFERRED EMBODIMENT

Figure 1:
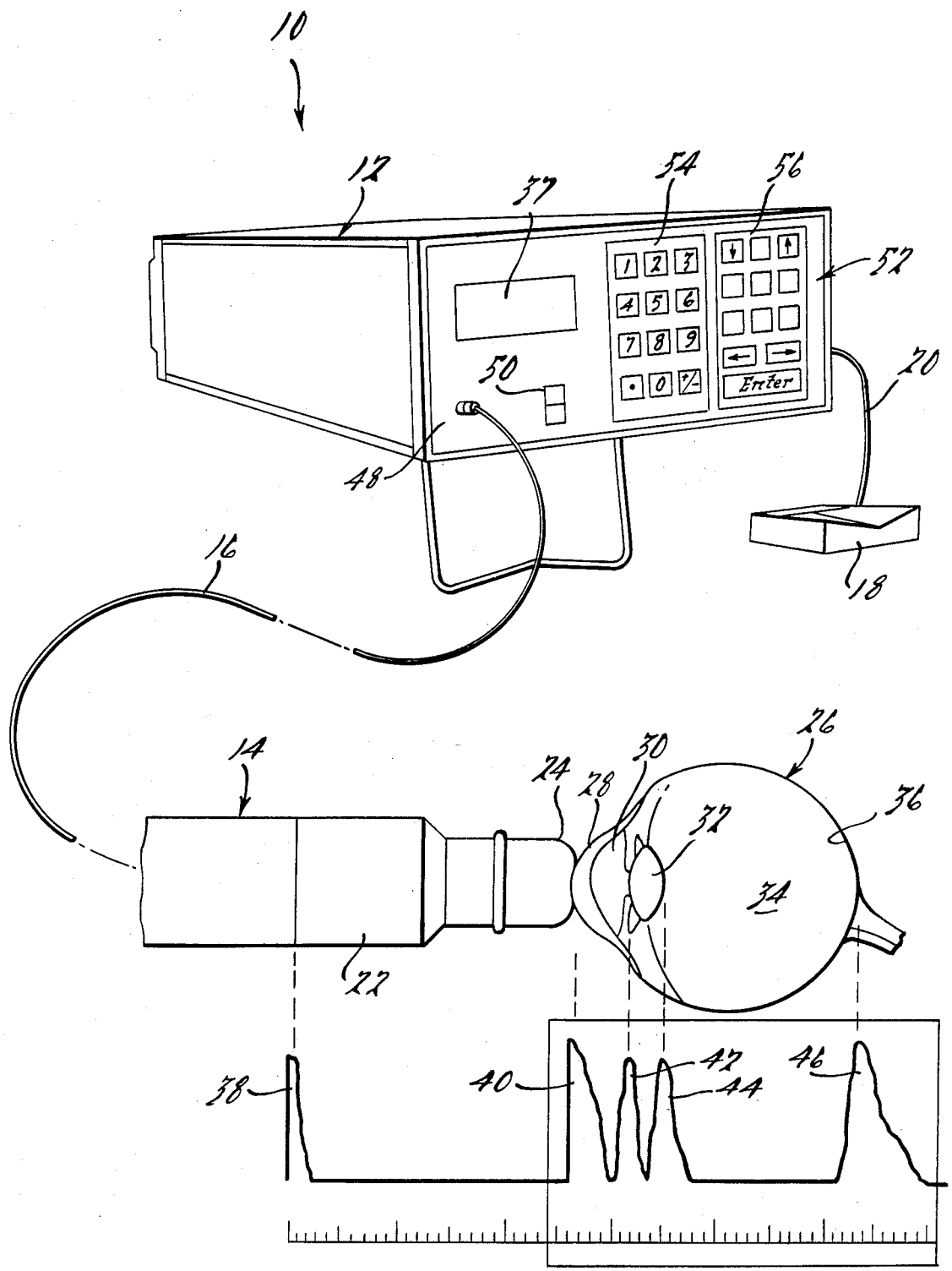
FIG. 1 is a perspective view of an ultrasonic system for obtaining ocular measurements according to the present invention.

Referring to FIG. 1, a perspective view of an ultrasonic system 10 according to the present invention is shown. The ultrasonic system 10 includes an ultrasonic diagnostic scanner 12, an ultrasonic probe 14 connected to the scanner 12 via cable 16, and a footswitch 18 connected to the scanner via cable 20 for permitting hand-free operation. The scanner 12 includes all of the circuitry required for the ultrasonic system 10, including a transmitter for generating an ultrasonic signal and a receiver for receiving echo signals from the transmitted ultrasonic signal, as will be more fully described below.

In order to obtain an ocular measurement, the transmitter in the scanner 12 generates a high voltage pulse which is sent to the probe 14 through cable 16. This pulse causes a piezoelectric transducer in the probe 14 to produce a short burst of ultrasonic frequency waves or vibrations out through a fluid chamber 22 and flexible membrane 24 of the probe 14 and into the eye 26 of the patient being examined. As the ultrasonic vibration proceeds through the eye 26, a portion of the vibration is reflected back to the probe transducer as the vibration encounters various tissue boundaries. Therefore, for example, a reflection of such ultrasonic vibration will be created when the burst of waves passes from the probe 14 to the cornea 28, from the aqueous region 30 to the lens 32, from the lens 32 to the vitreous region 34, and from the vitreous region 34 to the retina 36.

The transducer of the probe 14 then converts the echo reflections of the transmitted ultrasonic burst into electrical signals which are received and processed by the receiver in the scanner 12. One of the outputs from the scanner 12 which may be selected by the physician is an echo "histogram" display of the echo reflections on a dot matrix liquid crystal display 37 of the scanner 12. An echo histogram as used herein refers to a digital "picture" or frame frozen representation of the echo reflections which is not updated on a real-time basis, as in prior cathode ray tube displays. In accordance with the present invention, the data necessary to create the histogram is stored in the memory of the scanner 12, thereby permitting the histogram to be displayed at a time independent of the time when the echo reflections were received. Such an echo histogram is illustrated in FIG. 1 and is correlated to the various tissue boundaries of the eye 26.

The first spike 38 in FIG. 1 represents the axial position of the outer end of the probe tranducer from which the ultrasonic vibrations are transmitted, and will be referred to hereinafter as the "main bang". However, it should be noted that this spike does not form part of the histogram on the LCD display 37, but is identified herein to facilitate an understanding of the operation of the scanner circuitry. A second spike 40 indicates the axial position of the cornea 28 and represents the first echo of the ultrasonic burst. The second spike 40 also substantially corresponds with the axial position of the outermost surface of the probe flexible membrane 24. The third, fourth, and fifth spikes, 42, 44, 46, respectively, indicate the respective axial positions of the front surface of the lens 32 (and/or the iris), the back surface of the lens 32, and the retina 36.

By determining these critical axial dimensions, a physician or other medical practitioner may gain valuable and needed information about the physical configuration and condition of the eye 26. Such information may be used for treating the eye, for selecting the proper artificial lens in lens transplant surgery, or the like. It should be noted that the ultrasonic probe 14 is normally secured in use in a stand-type device which includes surfaces whose position is fixed relative to the probe and against which the patient rests his chin and forehead. Such devices are commonly referred to as slit lamp stands. A further description of the ultrasonic probe 14 may be found in the patent application entitled "Ultrasonic Probe", as identified above.

Figure 4:
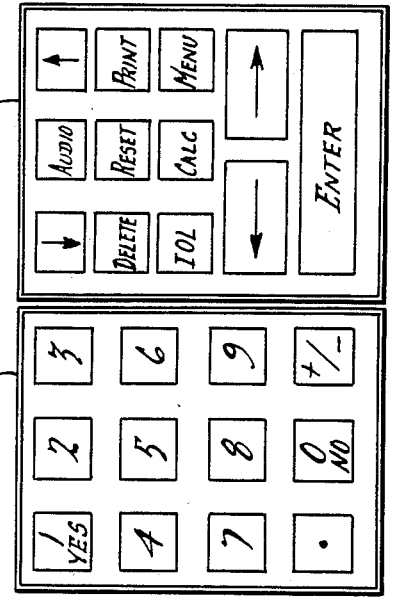
FIG. 4 is a front elevation view of the keypad shown in FIG. 1.

As illustrated in FIg. 1, the front panel 48 of the scanner 12 generally includes an ON/OFF switch 50, the liquid crystal display (LCD) 37, and a key board 52. The key board 52 is comprised of two key pads 54 and 56, which allow the user to enter and store data, select various menus of programs and information pre-programmed into the scanner 12, and control operational functions of the scanner 12. A more detailed illustration of the key board 52 is shown in FIG. 4, and will be more fully discussed below. The scanner may also be provided with a separate paper-tape printer (block 58 of FIG. 3) for creating permanent records of the numerical data and histogram displayed on the display 37.

Figure 2A:
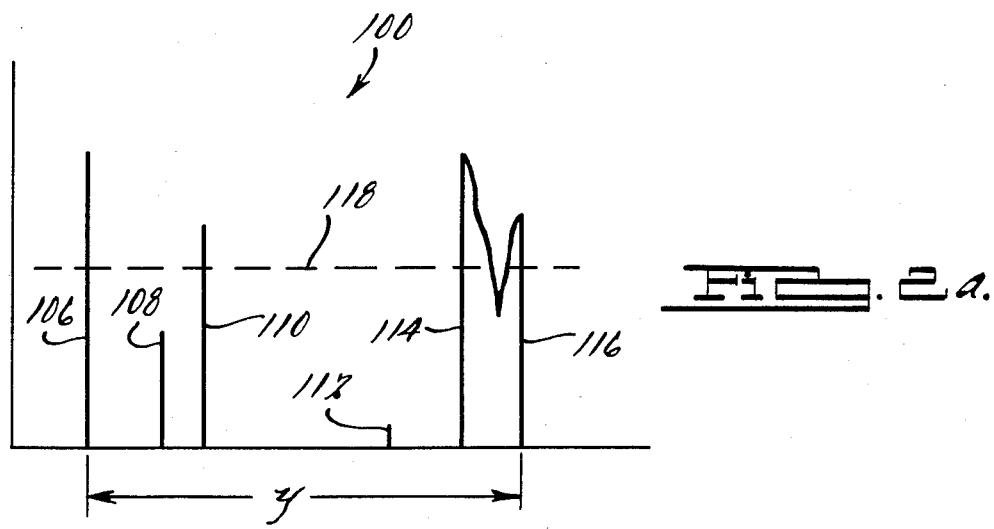
FIGS. 2a–c are echo graphs illustrating different measurement conditions.
Figure 2B:
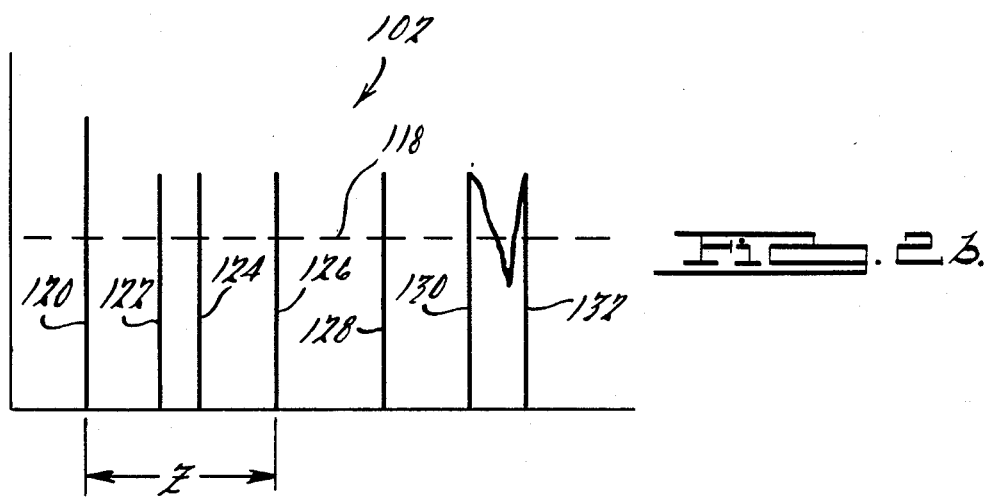
Figure 2C:
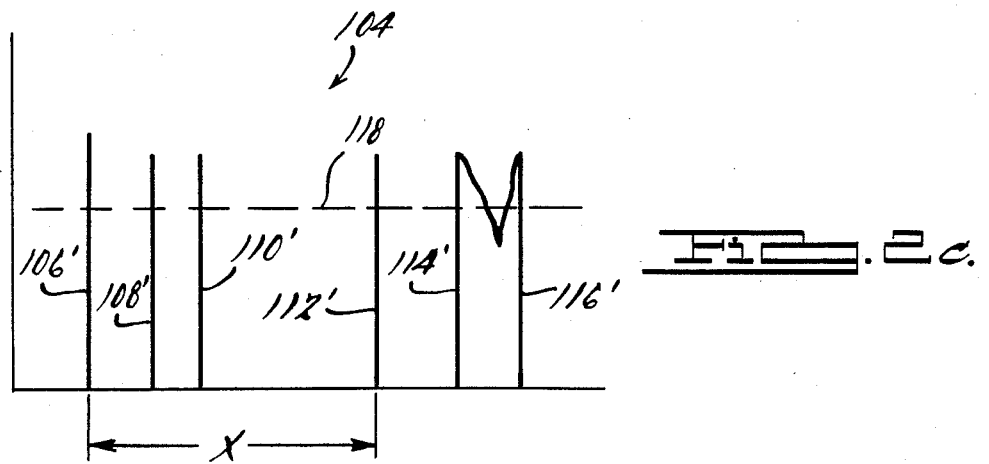

Referring now to FIGS. 2a–c, three schematic echo graphs 100–104 are shown. The first echo graph 100 (FIG. 2a) illustrates an axial misalignment condition, whereby the probe 14 is not in proper alignment with the eye 26. Such an axial misalignment may occur for example if the probe 14 is not properly centered on the eye 26 and/or the probe is tilted with respect to the eye.

In the echo graph 100, spike 106 represents the cornea, spike 108 represents the anterior lens, spike 110 represents the posterior lens, spike 112 represents the retina, and spikes 114–116 represent the sclera (an exterior coating of the eye). It should be noted that the amplitude of the retinal spike 112 is much smaller than the amplitude of the other spikes, and the amplitudes of the two lens spikes 108-110 are different. This echo graph should be compared with echo graph 104 of FIG. 2c, which represents a measurement during an axial alignment condition. Since each of the spikes in echo graph 104 represent the same tissue boundaries of the eye as in the echo graph 100, the spikes are identified with the same reference numerals primed. It should be noted that the magnitude of the retinal spike 112' is now comparable with the magnitudes of the other spikes, and the two lens spikes 108'-110' have approximately the same magnitude.

Both the echo graphs 100 and 104 include a dashed line 118 which represents the threshold level employed in traditional axial length measurement techniques. These techniques have typically relied upon pattern recognition algorithms which are based upon counting the number of spikes or echo signals with amplitudes above a predetermined threshold level. Since the cornea, lens and retina are well defined tissue boundaries, the echo reflections from these tissue boundaries will also be well defined and easily distinguishable from noise or insignificant reflections when the probe is properly aligned with the eye. Accordingly, if it is desired to measure the distance from the cornea to the retina, only the first four (4) significant echo signals are counted, that is the first four echo reflections which exceed a predetermined threshold level, and the time between the first and fourth echo signal is measured. This time value is then related to the distance or axial length value through well known equations which correlate the time value with the velocity at which the ultrasonic burst is transmitted through the eye.

Under the traditional approach outlined above, an accurate axial length "X" will be produced when the probe is properly aligned with the eye, as shown in FIG. 2c. However, as shown in FIG. 2a, this traditional approach could result in producing an inaccurate axial length "Y", because neither the anterior lens spike 108 nor the retinal spike 112 are above the threshold level 118. Thus, under the traditional approach, the fourth significant echo signal counted would be the second sclera spike 116 instead of the retina spike 112.

Another inaccurate axial length measurement could be produced with regard to the measurement condition shown in FIG. 2b. The echo graph 102 of FIG. 2b illustrates an ocular abnormality condition, such as may be caused by the presence of a tumor in the eye being examined. In the echo graph 102, spike 120 represents the cornea, spike 122 represents the anterior lens, spike 124 represents the posterior lens, spike 126 represents a tumor, spike 128 represents the retina, and spikes 130-132 represent the sclear. It should be noted that in this measurement condition, the probe is in proper alignment with the eye being examined. However, the presence of a tumor in the eye causes an additional echo reflection (spike 126) which exceeds the threshold level 134. Under the traditional axial length measurement technique outline above, an inaccurate axial length "Z" may be produced, since the fourth significant echo signal occurs at the initial boundary of the tumor.

In accordance with the present invention, the ultrasonic diagnostic scanner 12 employs a novel measurement technique which is capable of detecting axial misalignments and prevent the scanner 12 from producing an inaccurate axial length indicative output. As will be more fully described below, the scanner 12 examines not only which echo reflections exceed a certain threshold level, but also examines the temporal relationship between predetermined pairs of these echo reflections to determine whether or not the times between these predetermined pairs are within predetermined ranges.

The ultrasonic diagnostic scanner 12 also examines the temporal relationship between the "main bang" and the occurrence of the echo reflection representing the cornea. Thus, with reference to FIG. 1, the scanner 12 examines the time between the main bang 38 and the corneal spike 40. This examination is performed in order to detect a corneal depression condition, which may occur if the probe 14 is pressed too firmly against the eye 26. In such a situation, the flexible membrane 24 of the probe 14 will deform and thereby alter or decrease the time it takes for the corneal spike to occur with reference to the transmission of the ultrasonic burst (i.e. the main bang). As will be more fully described below, when the scanner 12 detects a corneal depression condition, it will generate a perceptible output which will inform the physician of the occurrence of this condition.

Referring now to FIG. 3, a block diagram of the ultrasonic system circuitry 150 contained in the ultrasonic diagnostic scanner 12 of FIG. 1 is shown. At the heart of the system is a microprocessor 152 which controls the functioning of the system circuitry 150 through appropriate command signals placed upon a system data bus 154. The system circuitry 150 includes a transmitter 156 for causing a transducer 158 to transmit an ultrasonic signal at a predetermined velocity. The transmitter 158 is responsive to a transmit command signal which is placed in the data bus 154 by the microprocessor 152. The transmit command signal is detected by a control logic circuit 160, which directs the command signal to the transmitter 156 along conductor 162.

The transducer 158 also serves to receive the echo reflections of the transmitted ultrasonic signal which result when the ultrasonic signal encounters the various tissue boundaries of the eye being examined, as discussed above. The transducer 158 then converts these reflected vibrations into electrical echo signals which are transmitted along a conductor 164 to a receiver circuit generally designated by reference numeral 166. It should also be noted that since the transmitter 156, the transducer 158 and the receiver circuit 166 are all connected to conductor 164, the receiver will also be able to detect the "main bang" when the ultrasonic signal is transmitted.

The receiver circuit 166 generally comprises an amplifier circuit 168, a mixer circuit 170, a low pass filter circuit 172, a peak detector circuit 174 and a threshold detector circuit 176. The gain of the amplifier circuit 168 is controlled by a sensitivity adjustment circuit which includes a digital-to-analog (D/A) converter 178. The sensitivity adjustment circuit operates in combination with the receiver amplifier circuit 168 to permit the scanner 12 to automatically adjust its sensitivity. Since the sensitivity of ultrasonic probes generally vary from probe to probe, it has been found necessary in some instances to "match" the probe to a particular scanner. However, the automatic sensitivity adjustment feature of the present invention eliminates the need for this procedure and insures that the receiver circuit will not be saturated when a very sensitive probe is employed.

In order to adjust the gain of the receiver amplifier circuit 168 and hence the sensitivity of the scanner 12, the microprocessor 152 will address the digital-to-analog converter 178 and place a sensitivity command signal on the data bus 154. The digital sensitivity command signal will then be converted to the appropriate analog value and transmitted to the receiver amplifier circuit 168 along a conductor 180. It should be understood that this sensitivity adjustment technique may also be applied to the transmitter side of the scanner 12 to effectuate the desired adjustment by controlling the transmitted power of transmitter 156.

The mixer circuit 170 of the receiver circuit 166 is connected to the dual outputs of the amplifier circuit 168 and performs a full wave rectification operation on the amplified echo signals. The rectified echo signals are then processed through low pass filter circuit 172, which eliminates the high frequency harmonics of these echo signals. When the echo signals are received, they each resemble a decaying sinusoidal energy burst which is highly compressed. The mixer circuit 170 rectifies the positive excursions of this energy burst, and the low pass filter circuit 172 produces a generally smooth envelope of this energy burst. A graphical representation of this envelope waveform is shown in connection with the flow chart of FIG. 8.

The output from the low pass filter circuit 172 is connected to both the peak detector circuit 174 and the threshold detector circuit 176. The threshold detector circuit 176 generally comprises a comparator which produces an "edge" signal on conductor 182 whenever the filtered echo signal exceeds a predeterminable threshold level. This threshold level is controlled by a threshold level adjustment circuit which includes digital-to-analog converter 184. The converter 184 is in turn controlled by the microprocessor 152, which causes the threshold level to be modified by addressing the converter 184 and placing a threshold command signal on the data bus 154. The digital threshold command signal is converted to the appropriate analog level by the converter 184 and sent to the threshold detector comparator as an input along conductor 186.

The peak detector circuit 174 operates to produce a short "peak" or "PK" pulse on conductor 188 at approximately the maximum amplitude of each echo signal which exceeds the predetermined threshold level set by the digital-to-analog converter 184. It should be understood that if the echo signal does not exceed the predetermined threshold level, then no peak signal will be produced by the peak detector circuit 174. Accordingly, it should be appreciated that the peak detector circuit 174 serves to identify the maximum or central point in the filtered echo signal envelope, and therefore permits the time at which the echo reflection occurred to be more precisely defined in comparision to the edge signal produced by the threshold detector circuit 176.

The peak and edge signals identified above are then sent to a programmable logic and timer circuit generally designated by reference numeral 190. The programmable logic and timer circuit 190 generally comprises the control logic circuit 160, a 10 MHZ timer/counter circuit 192, a pulse counter circuit 194 and a binary comparator circuit 196. The control logic circuit 160 receives both the peak and edge signals, as well as certain command signals from the microprocessor 152 via data bus 154. In response to the appropriate command signal from the microprocessor 152, the control logic circuit 160 determines whether the peak or the edge signals will be employed to control a counter contained in the timer/counter circuit 190.

When the main bang occurs, the control logic circuit 190 sends a strobe signal on conductor 198 at the appropriate time to the timer/counter circuit 192. As will be more fully described below, the timing of the strobe signal will depend upon what distance is to be measured. For example, the strobe signal could be issued upon receipt of the first peak signal (i.e., the peak signal representing the corneal reflection) or upon the detection of the main bang. The strobe signal causes the counter contained in the timer/counter circuit 192 to start counting at a 10 MHZ rate. This counting operation will continue until a halt signal is produced by the binary comparator circuit 196. The binary comparator circuit 196 is controlled by a pulse number command signal placed on the data bus 154 by the microprocessor prior to the transmission of the ultrasonic signal (i.e., the main bang).

When the axial length of the eye is to be measured, the microprocessor 152 will command the control logic circuit 160 to utilize the peak signals for stopping the counter contained in the timer/counter circuit 192. Accordingly, the control logic circuit 160 will permit the peak signals received on conductor 188 to be transmitted to the pulse counter 194 via conductor 199. If, for example, the distance between the cornea and the retina of the eye is to be measured, the microprocessor will cause a binary value corresponding to the numeral four (4) to be stored by the binary comparator circuit 196. Then, as the peak signals are received by the pulse counter circuit 194, they are counted and compared with the binary value stored by the binary comparator circuit 196. After four peak signals have been counted by the pulse counter circuit 194, the binary comparator circuit 196 will produce the halt signal on conductor 200, which will cause the counter in the timer/counter circuit 192 to stop counting.

Since the counter in the timer/counter circuit 192 was counting at a predetermined rate (i.e. 10 MHZ), the numeral value or count signal stored in the counter is indicative of the time between the transmission of the ultrasonic signal and the occurrence of the selected number of peak signals (i.e. 4). The count signal is then transmitted to the random access memory (RAM) portion of the computer memory 202, where the microprocessor will perform the necessary calculations to determine the axial length of the eye from equations stored in the read only memory (ROM) portion of the computer memory, as set forth below.

Figure 7:
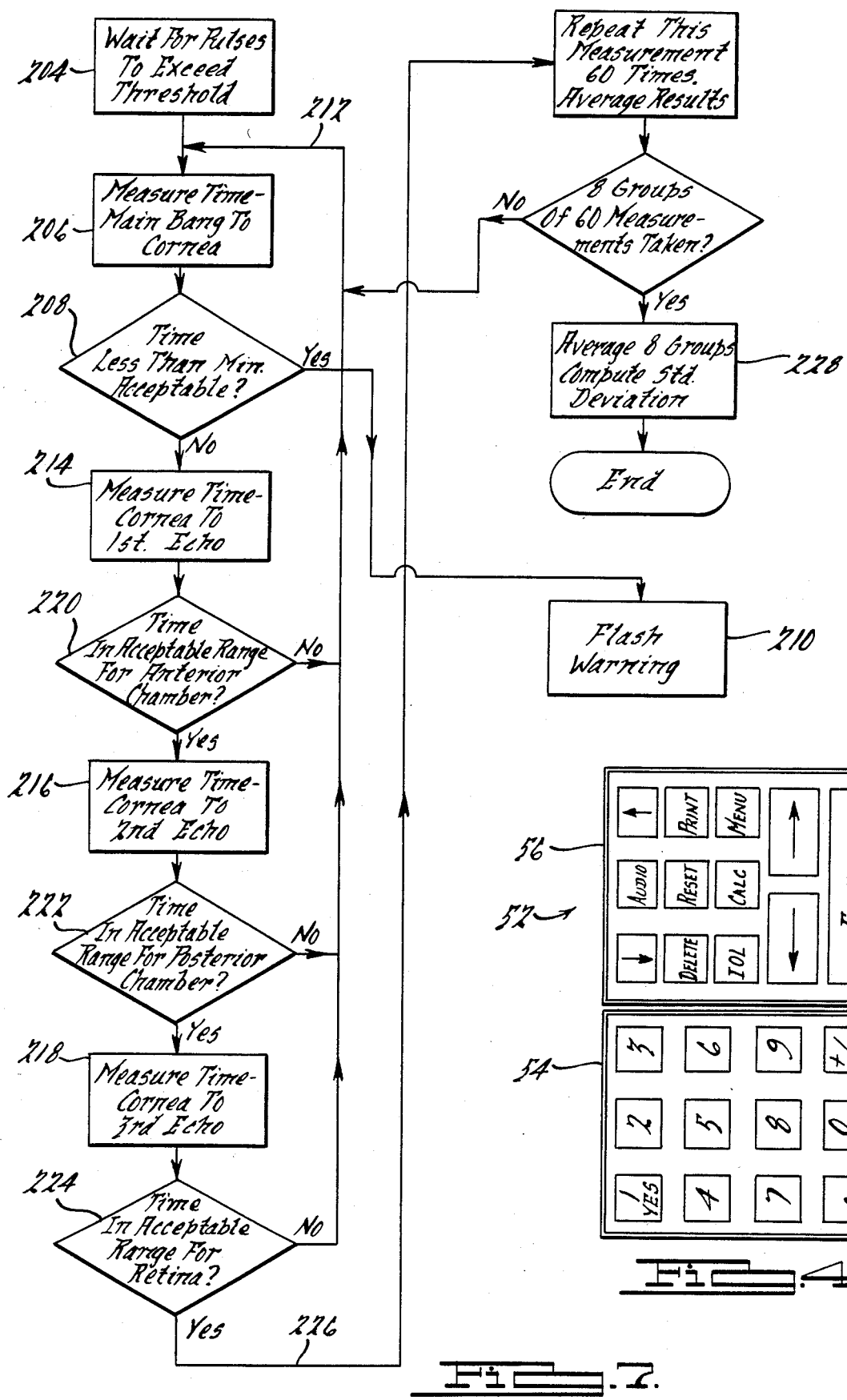
FIG. 7 is a flow chart of the method used to detect a corneal depression condition and an axial misalignment condition.

FIG. 7 illustrates a flow chart of the method employed in accordance with the present invention to measure the axial length of the eye. FIG. 7 also illustrates the preferred methods for determining a corneal depression condition and determining an axial misalignment condition. The first block 204 represents the point in the measurement procedure where the main bang has occurred, the counter contained in the timer/counter circuit 192 is counting, and the pulse counter 194 is waiting to receive the first peak signal.

Block 206 indicates that the scanner 12 first measures the time between the main bang to the cornea. As described above, this time is measured by the microprocessor 152 programming a binary "one" into the binary comparator 196 in order to stop the counter contained in the timer/counter 192 at the occurrence of the first peak signal (i.e., the peak signal due to an echo reflection at the cornea).

Diamond 208 represents the preferred technique for detecting a corneal depression condition. The time measured between the main bang and the cornea is examined to determine if it is less than a minimum acceptable time. This minimum acceptable time may be pre-programmed into the ROM memory of the scanner, but it is preferred for this time to be defined just prior to the time of measurement. For example, when the probe 14 is not in contact with the eye, an echo reflection will occur at the flexible membrane 24 and be detected by the scanner 12. The time it took for this echo reflection to occur could then be stored in the RAM portion of the memory 202 for later comparison with the time measured between the main bang and the cornea when the probe is in contact with the eye being examined. If the time of the corneal echo reflection is a predetermined percentage less than the time of the membrane reflection previously stored (or other appropriate algorithm), then a "yes" will result from diamond 208.

When the determination of diamond 208 produces a "yes", thereby signifying that a corneal depression has occurred, the microprocessor 152 will place a warning command signal on data bus 154 which will cause the LCD display 37 to flash or display a visibly perceptible message (block 210). This message will indicate to the operator that a corneal depression condition has occurred, so that the operator may make the appropriate adjustment to the position or pressure placed upon the probe 14.

Blocks 214–218 indicate that times between the occurrence of the corneal echo reflection and the next three peak signals are individually measured. After each of these measurements have taken place, diamonds 220–224 indicate that the temporal relationship between the corneal echo reflection or peak signal and the three following peak signals are examined. These temporal determinations represent the preferred method of detecting an axial misalignment condition.

Although ocular parameters will generally be different from patient to patient, certain ranges for selected parameters may nevertheless be defined. Thus, for example, the time between the corneal peak signal and the anterior lens peak signal should occur within a first predetermined range, the time between the corneal peak signal and the posterior lens peak signal should occur within a second predetermined range, and so forth. If the time between any of these peak signals is outside of their respective ranges, then the scanner 12 determines that an axial misalignment condition has occurred.

When an axial misalignment condition is detected, line 212 of FIG. 7 indicates that the measurements are repeated until the condition is corrected. It is important to note that the count signals produced by the counter in the timer/counter 192 are not used by the microprocessor 152 in any subsequent axial length calculations in order to prevent an inaccurate axial length output from the scanner 12.

It should also be noted that when this condition is detected, the microprocessor 152 may cause a tone to be emitted by a tone generator circuit 225. Conversely, the microprocessor 152 could also be programmed to cause the tone generator 225 to emit a specific tone only when an axial alignment condition exists after the measurement procedure has commenced. Thus, after the physician has depressed the footswitch 18 or otherwise initiated the measurement procedure, a tone will be generated to inform the physician that the probe 14 is properly aligned with the eye and the measurement of the axial length is proceeding.

Referring again to FIG. 7, line 226 indicates that when an axial alignment condition exists, the individual time measurements identified above are repeated a predetermined number of times, preferably sixty (60) times. For each of these measurements, the appropriate count signals are stored in the RAM portion of the memory 202, and after the group of sixty measurements have been completed, the microprocessor 152 calculates an average of these count signals. Then, as indicated by block 228, the group of sixty measurements is repeated another seven (7) times, until a total of eight (8) groups of measurements have been taken. The eight averaged count signals are then averaged again, and the resulting count signal is related to an axial length numerical value. This numerical value is then displayed on the LCD display 37. It should be appreciated that the number of masurements taken and averaging technique employed are used to enhance the accuracy of the axial length value produced by the scanner 12.

In one embodiment of the present invention, one of the programs stored in the ROM portion of the memory 202 also permits a standard deviation of the eight groups of measurements taken to be displayed as well. This standard deviation value will provide an indication to the physician of the steadiness of the probe position with respect to the eye being examined.

While the method of measuring and detecting the corneal depression and axial misalignment conditions described above represents the preferred method, it should also be appreciated that suitable variations may be made without departing from the principles involved. For example, the axial misalignment condition may be detected by comparing other times than those set forth above. Thus, it may be advantageous to compare the time between the occurrence of the anterior lens peak signal and the posterior lens peak signal, and so forth. Similarly, it may be advantageous to determine if a small echo signal occurs just before the scleral reflections, as shown in FIG. 2a. It is also important to note that the scanner 12 includes the capability of overriding or modifying these methods to account for such situations as an extra reflection due to the presence of a cataract, tumor, or the like. For example, through the keyboard, the physician will be able to program the number of echoes to be considered or select a particular threshold level to be employed.

It should also be noted that the system circuitry 150 of FIG. 3 includes a voice synthesizer circuit 230. This voice synthesizer circuit 230 may be utilized by the scanner 12 in several ways. For example, the microprocessor 152 could be programmed to cause the voice synthesizer circuit 230 to audibly recite the axial length and standard deviation values displayed on LCD display 37. The voice synthesizer circuit 230 may also be used to audibly recite various words, such as "ready" when the scanner 12 is ready to take a measurement, and so forth.

When an echo histogram is to be desplayed on the LCD display 37 of the scanner 12, the microprocessor 152 will command the control logic circuit 160 to utilize the edge signals for stopping the counter contained in the timer/circuit 192. Accordingly, the control logic circuit 160 will permit the edge signals received on conductor 182 to be transmitted to the pulse counter 194. The microprocessor will also cause a binary value to be stored in the binary comparator 196 which corresponds to the number of edge signals to be examined.

Referring to FIG. 8, a flow chart is shown which illustrates the preferred method for displaying an echo histogram according to the present invention. A graphical representation 232 of the filtered echo signals (which are sent to the peak detector 174 and the threshold detector 176) is also shown to facilitate an understanding of the method involved.

The graphical representation 232 includes a dashed line 234 to represent the threshold level, and the echo signal envelope 236. The first excursion 238 of the envelope 236 represents the corneal reflection, the second excursion 240 represents the anterior lens reflection, the third excursion 242 represents the posterior lens reflection, and the fourth excursion 244 represents the retinal reflection. The points 246–260 represent the eight points where the envelope 236 crosses the threshold level 234.

Each time the envelope 236 crosses the threshold level 234, the edge signal on conductor 182 in FIG. 3 will change logic states. Thus, at point 246, the edge signal will switch from a LO signal state to a HI signal state, and at point 248, the edge signal will switch again to its LO logic state. These changes in the edge signal are used by the control logic circuit 160 to control the counter contained in the timer/counter circuit 192. Accordingly, the precise points where the envelope 236 crosses the threshold level may be determined and stored in the RAM portion of the memory 202. By measuring when these crossing points occur at specific threshold levels, a map of the envelope 236 may be created.

Thus, in accordance with the present invention, the threshold level is adjusted to certain predetermined levels, and at each level the times at which the envelope crosses the threshold level is determined. In the scanner 12, these predetermined threshold levels are defined generally by the resolution of the LCD display 27. Although the LCD display 37 is a thirty two (32) row by eighty (80) column matrix dot display, the microcomputer 152 is programmed to resolve sixteen (16) different threshold levels. It may also be noted at this point that the LCD display used in the embodiment disclosed herein is an Epsom model EGY84320AT display.

Referring again to FIG. 8, the threshold level 234 is first reset at zero after the echo histogram program is initialized, as indicated by block 262. Block 264 indicates that the threshold level 234 is then incremented to the next higher level, which at this point is the lowest threshold level capable of being displayed on LCD display 37. Block 266 indicates that the pulse number stored in the binary comparator 196 is then reset to zero. This pulse number is subsequently incremented (block 268) so that the counter contained in the timer/counter circuit 192 will stop at the occurrence of the first edge signal received. Additionally, block 268 indicates that the control logic circuit 160 may also change the edge signal to be detected such that the counter contained in the timer/circuit 192 may be halted when the edge signal switches to a LO logic state, as well as when the edge signal switches to a HI logic state.

The counter in the timer/counter circuit 192 is then reset to zero (block 270), and the microprocessor 152 commands the transmitter 156 to produce a pulse which will cause the transducer to generate an ultrasonic signal (block 272). Block 272 also indicates that the microprocessor 152 will command the control logic circuit 160 to enable the counter contained in the timer/counter circuit 192 to begin counting at the appropriate point in time. For example this point in time could be the occurrence of the first peak signal.

When the number of edge signals counted by the pulse counter 194 equals the pulse number stored in the binary comparator 196, block 274 indicates that the value of the current threshold level is stored in a RAM memory location which corresponds to the count signal determined by the timer/counter circuit 192. Line 276 indicates that the pulse number is incremented to the next higher number, and the measurement is repeated again.

This process continues until each point where the envelope 236 crosses the current threshold level has been examined. This determination is made with reference to diamond 278. After the last crossing point has been detected, the binary comparator 196 will be looking for an edge signal which does not exist. Consequently, the counter in the timer/counter circuit 192 will continue counting until the count has reached the maximum value of the counter. At this point, the microprocessor 152 determines whether or not the threshold level has been incremented to its maximum value (diamond 280). If not, then line 282 indicates that the threshold level 234 will be incremented to the next higher value, and the process described above will be repeated until all of the crossing points at the new threshold level have been detected.

When the entire process has been repeated at each of the resolvable threshold levels, the RAM portion of the memory 202 will contain a map of the envelope 236, which may then be displayed in response to an appropriate command signal issued by the microprocessor. While the above method represents the preferred method of displaying an echo histogram according to the present invention, it should be appreciated that this method may be varied without departing from the principles disclosed. For example, instead of the threshold level being upwardly adjusted during this procedure, it could also be downwardly adjusted from a maximum threshold level as well. It should also be noted that it may be advantageous to create an echo histogram concomitantly with the measurement of the axial length of the eye. Additionally, it may be advantageous to update the histogram periodically or continuously under the appropriate circumstances.

It should also be understood that in order for the scanner 12 to display an accurate histogram of the echo reflections, it is necessary for the rate at which the histogram is created to be sufficiently faster than the rate at which the echo reflections change, so that the resultant histogram is equivalent to a histogram created during a single sweep period. While it may be desirable in some instances to provide a cathode ray tube display of the echo reflections, it should be appreciated that the digitally created histogram according to the present invention provides an inexpensive alternative to the former type of display while retaining substantialy all of its advantages.

Referring to FIG. 4, a front elevation view of the keyboard 52 is shown. The keyboard 52 is shown to comprise a numeric keypad 54 and a control keypad 56. The control keypad 56 includes an "audio" key which is used to control the volume of the audible tones and speech produced by the scanner in cooperation with the two vertical arrow keys adjacent to the "audio" key. The "delete" key is used to erase the last character entered from the numeric keypad 54. The "reset" key is used to command the scanner 12 to revert to the previous mode of operation which the scanner was in before the "reset" key was in. The "print" key is used to command the scanner 12 to enable the printer 58 to record the data presented on the LCD display 37.

The "IOL" key of the control keypad 56 is used to call up on the LCD display 37 a menu listing the IOL formulas stored in the memory of the scanner 12. The "calc" key is used to command the scanner 12 to calculate the answer to an IOL or other appropriate formula selected. The "menu" key is used to initiate a menu mode in which one or more menus may be displayed on LCD display 37. The two horizontal arrow keys are used to control the position of two cursors presented on the LCD display 37. These cursors may be employed, for example, in connection with a histogram displayed on the LCD display 37 to identify two specific echo reflections for which a calculation of the axial distance therebetween is desired. Finally, the "enter" key is used to enter any selected numerical values in the RAM memory of the scanner 12.

Figure 5A:
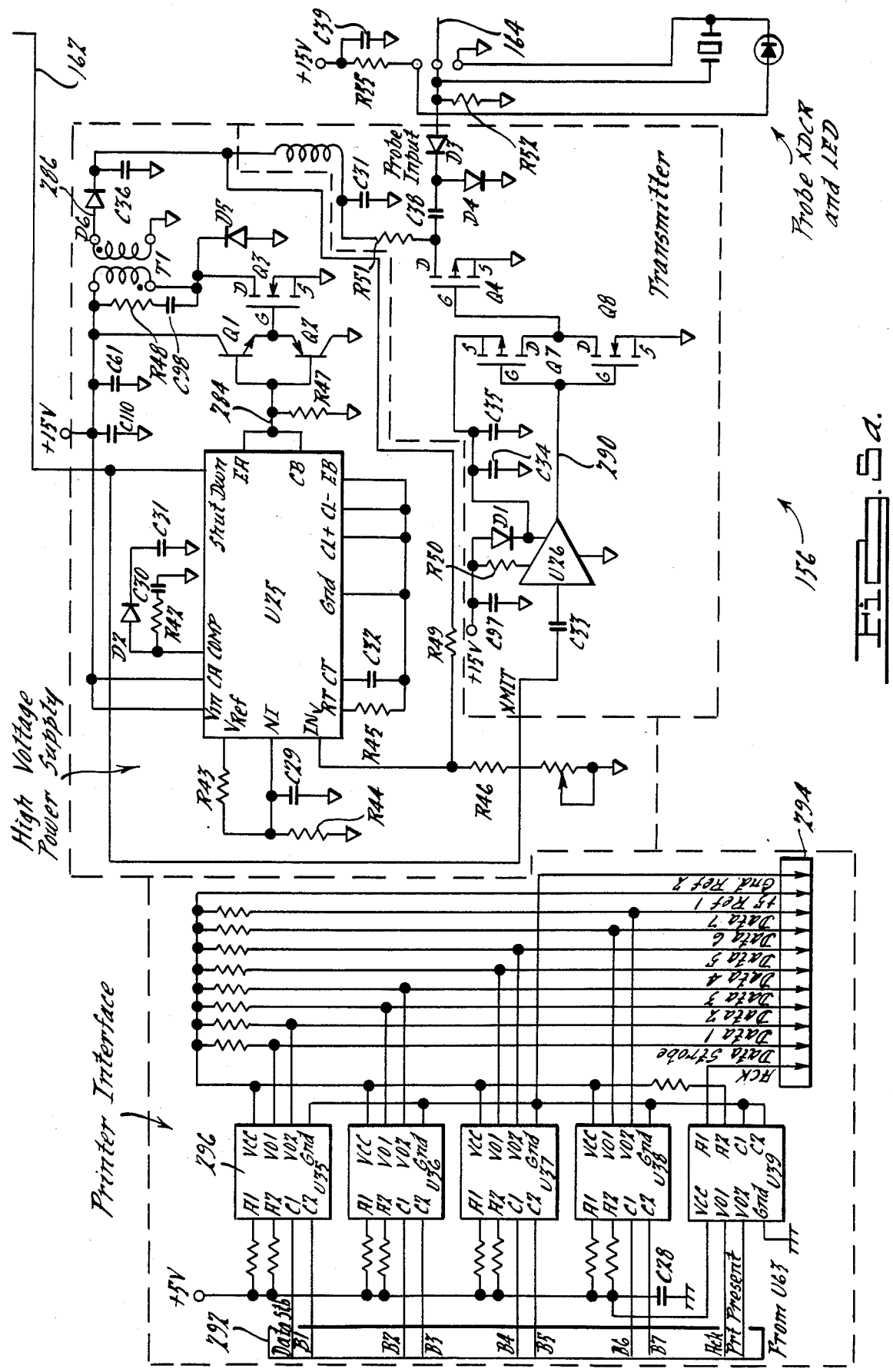
FIG. 5a is a schematic diagram of the transmitter shown in FIG. 3.

Referring now to FIG. 5a, a schematic diagram of the transmitter 156 is shown. The transmitter 156 receives the transmit command signal from the control logic circuit 160 along conductor 162. The transmit command signal is connected both to a switching voltage regulator U25 and a level shifting circuit U26. The switching voltage regulator U25 is used to generate a high D.C. voltage (i.e. 250 volts) from a low D.C. voltage input (i.e. 15 volts). The switching voltage regulator produces a pulse output on conductor at a frequency determined by R45 and C32. This pulse output controls the switching of transistors Q1-Q3. The transistor Q3 controls the passage of current through transformer T1, such that when the current through transformer T1 is stopped, the transformer will produce a high voltage output on conductor 286. This high voltage charges capacitor C36, which then operates in combination with diode D6 to clamp the voltage on conductor 288 to a high D.C. voltage level. Concomitantly, a capacitor C38 is slowly charged to this high D.C. voltage level through R51 and D4.

The level shifting circuit U26 operates to shift the 0.0 to 5.0 volt input on conductor 162 to a 0.0 to 15.0 volt output on conductor 290. When the transmit command signal is received on conductor 162, the output of the level shifting circuit U26 will enable F.E.T. transistor Q4 to conduct. This will cause the capacitor C38 to discharge rapidly through a resistor R52, which is connected across the probe transducer 158. This in turn produces a high voltage pulse across the transducer 158, which will cause the transducer to generate a short ultrasonic signal at a frequency of approximately 10 MHZ.

It should also be noted that the transmit command signal is also sent to the "shut down" port of the switching voltage regulator U26. Thus, the transmit command signal will cause the switching voltage regulator U25 to turn off during a measurement to insure that no high voltage pulse interferes with the accuracy of the measurement.

FIG. 5a additionally illustrates the interface from the microcomputer (port 292) to the printer 54 (port 294). This interface includes a plurality of opto-couplers 296, which are used to isolate the printer from the microcomputer circuitry.

Figure 5B:
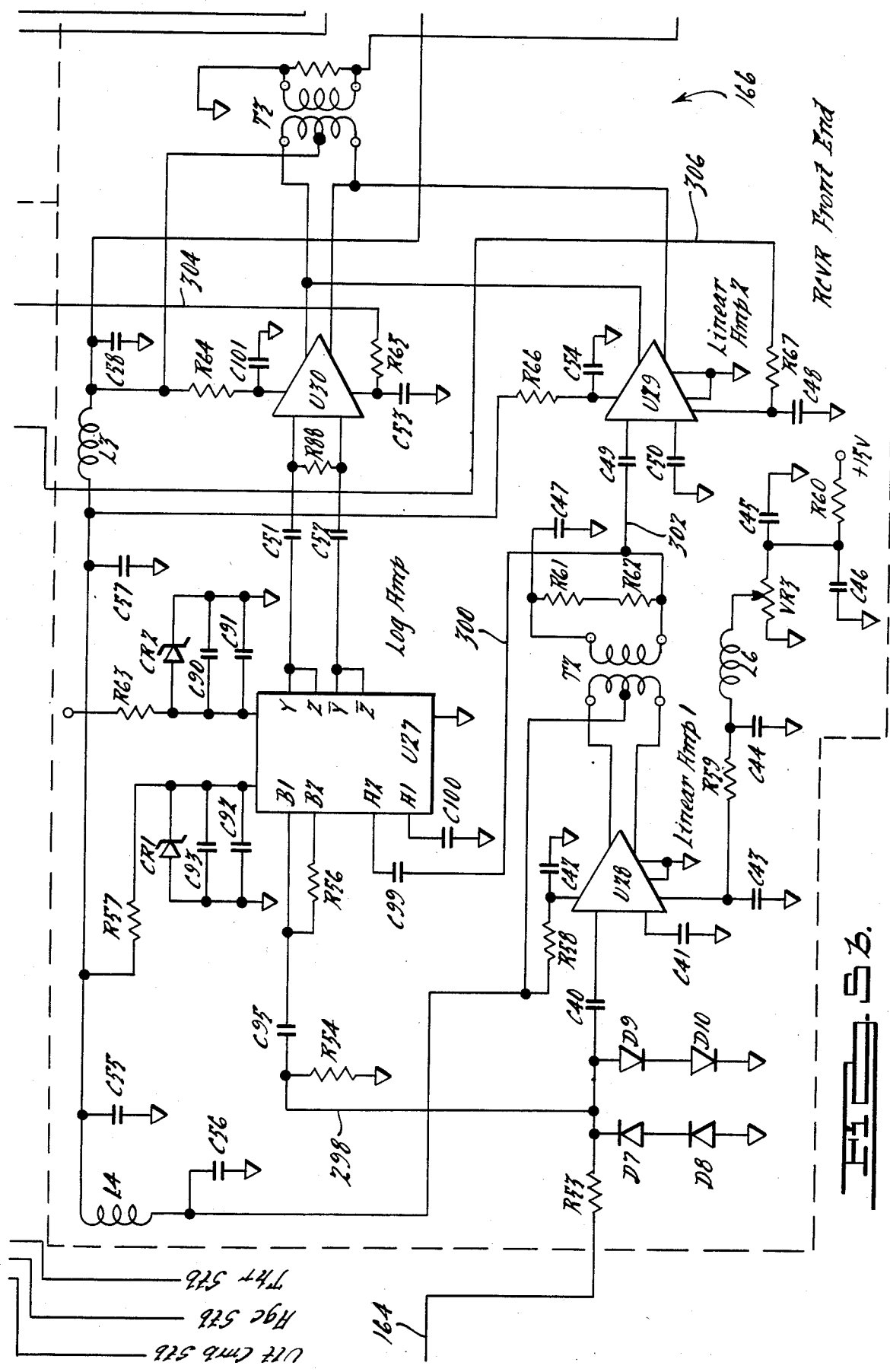
FIG. 5b is a schematic diagram of the front portion of the receiver shown in FIG. 3.

Referring to FIG. 5b, a schematic diagram of the front portion of the receiver circuit 166 is shown. This receiver circuit 166 is connected to the transducer 158 via conductor 164. The conductor 164 is in turn connected to a linear amplifier U28 and a logarithmic amplifier U27 (via conductor 298). However, it should be noted that diodes D7-D10 serve to clamp the high and low voltage level inputs to these circuits to a maximum of 1.5 volts and a minimum of −1.5 volts in order to protect the circuits from the high voltage induced at the main bang.

The linear amplifier U28 amplifies the decaying sinusoidal echo signals received on conductor 164, and produces a differential output. This differential output is connected to an impedance matching transformer T2, which produces an amplified echo signal on conductors 300 and 302. Conductor 300 is connected to the logrithmic amplifier U27. Thus, there are two inputs into logarithmic amplifier U27, the unamplified echo signal on conductor 298 and the amplified signal on conductor 300. The logarithmic amplifier U27 internally combines these two inputs to provide a second state of amplification.

The differential output from the logarithmic amplifier U27 is connected to a linear amplifier U30, which provides a third stage of amplification. This third stage of amplification is important because the gain of this stage is controlled by the sensitivity adjustment circuit discussed above via conductor 304. The output from the linear amplifier U30 is connected to an impedance matching transformer T3, which is in turn connected to the mixer circuit 170 shown in FIG. 5c.

It should be noted that the output from the transformer T2 is also connected to a linear amplifier U29 via conductor 302. This amplifier is used instead of linear amplifier U30 if the scanner is used to measure the corneal thickness of the eye. Since the probe used to measure corneal thickness has a sensitivity differing from the probe used to measure axial length, a different amplification technique must be employed. However, it is important to note that the gain of linear amplifier U29 is also controlled by the sensitivity adjustment circuit via conductor 306.

Figure 5C:
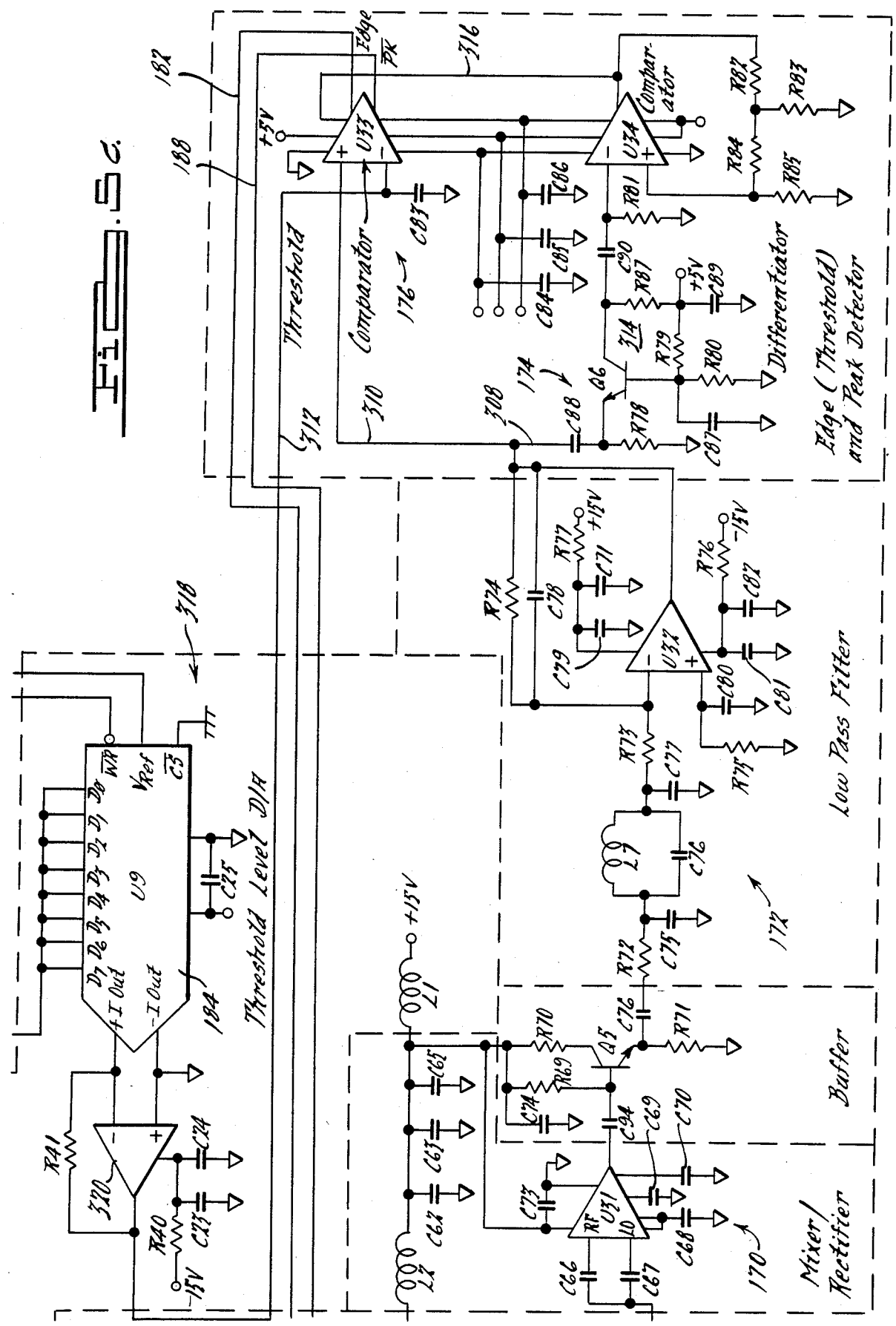
FIG. 5c is a schematic diagram of the remaining portion of the receiver shown in FIG. 3, as well as the threshold level adjustment means according to the present invention.

Turning now to FIG. 5c, a schematic diagram of the remaining portions of the receiver circuit 166 are shown. The mixer circuit 170 is shown to generally comprise a balanced mixer U31, which serves to rectify the amplified echo signals. Transistor Q5 is connected in an emitter-follower configuration which provides for a high input impedance, and operates as buffer between the balanced mixer U31 and the low pass filter circuit 172.

The output from the low pass filter 172 is connected to both the peak detector circuit 174 via conductor 308 and to the threshold detector circuit 176 via conductor 310. The threshold detector circuit 176 is shown to generally comprise a comparator U33, which operates to produce a HI logic edge signal on conductor 182 whenever the filtered edge signals exceed the predetermined threshold level. The threshold level is transmitted to comparator U33 from the threshold level adjustment circuit via conductor 312.

The peak detector circuit 174 comprises a differentiator circuit generally designated by reference numeral 314, and a comparator U34. The differentiator circuit 314 produces an output proportional to the slope of the filtered echo signals, and thereby produces a zero voltage level input to the comparator U34 when the filtered echo signal changes from a positive to a negative slope (at approximately its maximum amplitude). This zero voltage level input will cause the comparator U34 to produce a HI logic pulse on conductor 316. The conductor 316 is tied to an internal NAND gate in the comparator U33, which will result in a LO logic peak signal pulse produced on conductor 188 when the maximum amplitude of the filtered echo signal is above the threshold level.

FIG. 5c also illustrates a schematic diagram of the threshold level adjustment circuit 318. The threshold level adjustment circuit 318 comprises the D/A converter 184 and an op amp 320. The D/A converter 184 converts the digital threshold level command signal on the data bus 154 to an analog current output. This analog current output is connected to the op amp 320, which converts the analog current value to an analog voltage value on conductor 312.

Referring to FIG. 5d, a schematic diagram of the sensitivity adjustment circuit 322 is shown. The sensitivity adjustment circuit comprises the D/A converter 178, a current to voltage converting op amp U8, and an analog switch U14. The analog switch U14 is used to select which of the two linear amplifiers U29 and U30 in the receiver circuit 166 will be employed to amplify the echo signals. The analog switch operates to clamp one of these amplifiers and transmit the appropriate analog voltage values from op amp U8 to the other amplifier in response to an appropriate switching signal on conductor 324. The switching signal is transmitted by the control logic circuit 160 in response to an appropriate command from the microprocessor 152.

FIG. 5d also illustrates a schematic diagram of the voice synthesizer circuit 230 and the tone generator circuit 225. The voice synthesizer circuit 230 comprises a D/A speech controller circuit U11 and two memory circuits U12–U13. The controller circuit U11 operates in response to various command signals from the microprocessor 152 to address the memory circuits U12–U13, and produce an analog speech signal on conductor 326. The memory circuits U12–U13 are pre-programmed with certain sounds and words desired to be audibly produced by the scanner 12 under the appropriate circumstances.

The output from the voice synthesizer circuit 230 on conductor 326 is connected to a volume control circuit 328. The volume control circuit 328 includes a low pass filter 330, a D/A converter U6, and a current to voltage converting op amp U2. The volume control circuit 328 also includes a speaker driver circuit U5 and a speaker 332, both of which are shown in FIG. 5e. The D/A converter U6 is responsive to the appropriate volume control command signals placed upon the data bus 154 by the microprocessor to adjust the volume of the speech produced by the speaker 332.

The tone generator circuit 225 is shown to comprise a tone circuit U10, which is also connected to the low pass filter 330 of the volume control circuit 328. The tone circuit U10 is responsive to the appropriate tone command signals placed upon the data bus by the microprocessor 152 to produce an analog voltage signal which will cause the speaker 332 to produce the specific tones desired.

Referring to FIG. 5e, a schematic diagram of the programmable logic and timer circuit 190 is shown. The control logic circuit 160 of the programmable logic and timer circuit is shown to comprise a programmable logic array (PAL) circuit U23 and a flip flop circuit U24. The flip flop circuit U24 is responsive to various command signals on the data bus 154 to produce certain signals, such as the transmit command signal on conductor 162. The PAL circuit U23 receives the edge and peak signals on conductors 182 and 188, respectively, and selectively utilizes these signals to control the timer/counter circuit 192.

It should be noted that the PAL circuit U23 is programmed to produce several signals in accordance with the following equations:

$$\text{Strobe} = \text{Part } 1 + \overline{\text{SG}}.\text{Bang}$$

$$\text{Part } 1 = \text{Peak}.\text{Meas}.\text{PK} + \overline{\text{Peak}}.\overline{\text{En}}.\text{Meas}.\text{PK}.\text{SG} + \overline{\text{Peak}}.\text{En}.\text{Thr}$$

$$\text{Echo} = \overline{\text{Peak}}.\text{PK} + \text{Peak}.\overline{\text{Thr}} = \overline{(\text{Peak}+\text{PK})}.\overline{(\text{Peak}+\text{Ths})} = \overline{\text{Peak}}.\text{PK} + \text{Peak}.\overline{\text{Thr}} + \text{PK}.\overline{\text{Thr}}$$

$$\text{Thr} = \text{Edge}.\text{Positive Edge}.\text{En} + \text{Edge}.\text{Positive Edge}.\text{En},$$

where the symbol "+" indicates a logic "OR", and the symbol "." indicates a logic "and". Thus, for example, the "strobe" signal will be produced whenever a "Part 1" signal occurs, or whenever the combination of a "$\overline{\text{SG}}$" signal and a "Bang" signal occurs. The "$\overline{\text{SG}}$" signal indicates that the counter contained in the timer/counter circuit 192 should start counting upon the occurrence of the main bang, while a "SG" signal indicates that the counter should start counting upon the occurrence of the first peak signal. The "Bang" signal indicates that the main bang has occurred.

Additionally, the "positive edge" signal indicates that the pulse counter U19 should count edge signals which switch from a LO logic state to a HI logic state, whereas a "positive edge" signal indicates that the edge signals which switch from a HI logic state to a LO logic state should be counted. The "Peak" signal indicates that the pulse counter U19 should count peak signals rather than edge signals.

The timer/counter circuit 192 comprises a 10 MHZ clock U15, latch circuit U18, and a sixteen bit counter. The sixteen bit counter is comprised of counter circuit U17 for the four least significant bits, JK flip flop U16 for the fifth bit, and a portion of a counter circuit U59 (shown in FIG. 6b) for the remaining eleven bits. While the present embodiment disclosed provides for only one counter in the time/counter circuit 192, it should be appreciated that a plurality of counters could also be employed to concomitantly produce a plurality of count signals.

The pulse counter circuit 194 comprises a pulse counter U19 and a D-type flip flop U22, which is used to reset the pulse counter U19. Finally, the binary comparator circuit 196 is shown to comprise binary comparator U20, a latch U21, a JK flip flop U16, and a D-type flip flop U22.

Briefly reviewing the operation of the programmable logic and control circuit 190, the microprocessor 152 will command the PAL circuit U23 to transmit either the edge or peak signals on conductor 199. Taking a measurement of the axial length for example, the PAL circuit U23 will transmit the peak signals on conductor 199 as they are received from conductor 188. The microcomputer 152 will place a selected pulse member on the data bus 154 which will be stored by latch U21. When the transmit command signal is decoded by the flip flop circuit U24, the pulse counter U19 and the timer/counter circuit counter will be reset. Then, when the main bang (SG=0) or first peak (SG=1) is detected by the PAL U23, a strobe signal will be produced on conductor 198. This will cause the output of flip flop U22 to change states and start the counter U17 to start counting.

If, for example, the pulse number stored by the latch U21 is a binary "one", then the binary comparator U20 will cause a LO logic signal to be produced on conductor 334 following the first HI to LO echo bar transition. This signal will cause the output of flip flop U22 to again change states and produce a halt signal on conductor 200 following the next strobe to HI transition. The halt signal will cause the counter in the timer/counter circuit 192 (i.e. circuits U16, U17, and U59) to stop counting. Upon receipt of the "gate LO" command signal on conductor 336, the latch U18 will place the five least significant bits of the count signal produced by the counter on the data bus 154.

It should also be noted that FIG. 5e also illustrates a schematic diagram of the reset circuitry 338 for the system circuitry 150.

Figure 6C:
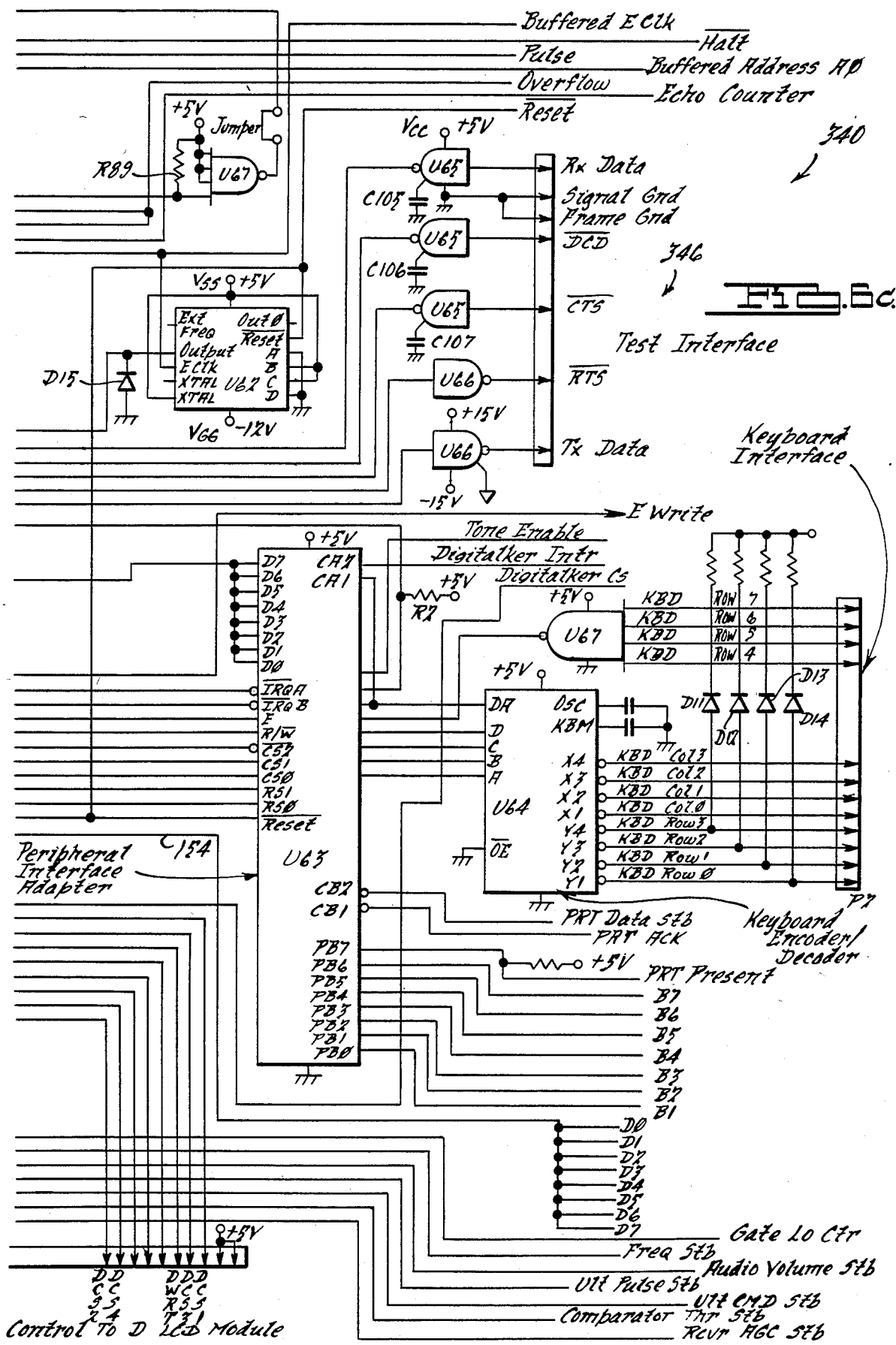

Referring now to FIGS. 6a–c, a schematic diagram of the microcomputer circuitry 340 according to the present invention is shown. The microcomputer circuitry 340 includes the microprocessor 152 (or central processing unit U40). While a Motorola MC6809 eight-bit microprocessor chip is utilized in the embodiment disclosed, it should be understood that any suitable microprocessor or minicomputer chip may be employed in accordance with the present invention. The data ports of the microprocessor 152 are labeled D0–D7, while the address ports are labeled A0–A15. A plurality of buffers U41–U43 are employed to grab each set of data and address signals as they are generated by the microprocessor 152. The output of the buffer U43 provides the data bus 154, while the combined outputs of the buffers U41–U42 provide an address bus 342.

The microcomputer circuitry 340 also includes four ROM circuits U44–U45 and U47–U48, the first three of which hold 8K bytes of memory and are used to store the system software. ROM circuit U48 contains a commercial arithmetic software package. The microcomputer circuitry 340 also provides for two non-volatile memory circuits U54 and U57, which are used to store such parameters as the velocity of sound, and so forth. For the RAM portion of the system memory, two RAM memories U51–U52 each provide for 2K bytes storage capability. It should be noted that each of these memory circuits are tied to a memory data bus 343, which interfaces with the system data bus 154 via a buffer U55.

FIG. 6a also illustrates the memory map decoder logic circuits U46, U49 and U53. These circuits are used to address specific locations in the various memory circuits described above. A decoder/demultiplexer circuit U50 is also shown, which is used to produce the signals necessary to address certain circuits operating under the control of the microprocessor 152. For example, the decoder/demultiplexer circuit U50 operates to produce a "AGC STB" signal on conductor 344 which is used to address the D/A converter 178 of the sensitivity adjustment circuit 322.

Referring to FIG. 6b, the microcomputer circuitry is shown to include three latch circuits U56, U58, and U61. These latch circuits are each tied to the data bus 154, and are used as an interface between the data bus and the LCD display 37. FIG. 6b also illustrates a universal asynchronous receiver-transmitter (UART) circuit U60, which together with a baud rate generator circuit U62 (shown in FIG. 6c) form part of a test interface circuit 346 used for maintenance purposes.

Referring to FIG. 6c, a peripheral interface adapter (PIA) circuit U63 is shown. This PIA circuit U63 is used to control the printer 54. The PIA circuit U63 is also used in cooperation with a decoder/driver circuit U64 to receive data from the key board 52 and transmit this data to the memory data bus 343.

In order to facilitate a further understanding of the circuits employed in the system circuitry 150, the following table identifies each of the integrated circuit part numbers and many of the component values in the system circuitry.

TABLE

| | | | | | |
|---|---|---|---|---|---|
| U1 | LM385 | U2 | LM324 | U3 | LM339 |
| U4 | LM317 | U5 | LM386 | U6 | AD7524JN |
| U7 | AD7524JN | U8 | CA3240E | U9 | AD75254JN |
| U10 | CDP1863C | U11 | MM54104 | U12 | MM52164 |
| U14 | MC14052B | U15 | 10MHz | U16 | 74L576 |
| U18 | 74L5373 | U19 | 75L5393 | U20 | DM8131 |
| U21 | 74L5374 | U22 | 74L574 | U23 | PAL12H6CN |
| U24 | 74L5374 | U25 | LM3524 | U26 | DS0056 |
| U27 | TL441 | U28 | MC1350 | U29 | MC1350 |
| U30 | MC1350 | U31 | TL442 | U32 | LM318 |
| U33 | LM361 | U34 | LM361 | U35 | HCPL2730 |
| U36 | HCPL2730 | U37 | HCPL2730 | U38 | HCPL2730 |
| U39 | HCPL2730 | U40 | MC6809 | U41 | 74L5244 |
| U42 | 74L5244 | U43 | 74L5245 | U44 | MCM68764 |
| U45 | MCM68764 | U46 | PAL10L8 | U47 | MCM68764 |
| U48 | MC68A39 | U49 | PAL10L8 | U50 | 74LS138 |
| U51 | HM6116 | U52 | HM6116 | U53 | PAL10L8 |
| U54 | XD2210 | U55 | 74L5245 | U56 | 74L5374 |
| U57 | XD2210 | U58 | 74L5374 | U59 | MC6840 |
| U60 | MC6850 | U61 | 74L5374 | U62 | MM5307 |
| U63 | MC6821 | U64 | MM74C922 | U65 | 1489 |
| U66 | MC1488 | U67 | MC14012 | | |
| R1 | 1K | R2 | 10K | R3 | 27K |
| R4 | 10K 1% | R5 | 10K 1% | R6 | 4.7K |
| R7 | 6.98K 1% | R8 | 4.7K 1% | R9 | 1M 1% |
| R10 | 10K | R11 | 100K | R12 | 10K |
| R13 | 10K | R14 | 1M | R15 | 100K |
| R16 | 100K | R17 | 1M | R18 | 470Ω |
| R19 | 2.7K | R20 | 50K | R21 | 330K |
| R33 | 1M | R34 | 10K | R35 | 6.2K |
| R36 | 20K | R37 | 100Ω | R38 | 4.7K |
| R39 | 10K | R40 | 100Ω | R41 | 20K |
| R42 | 30K | R43 | 4.7K | R44 | 4.7K |
| R45 | 9.1K | R46 | 9.1K | R47 | 1K |
| R48 | 1K | R49 | 1M | R50 | 1K |
| R51 | 33K | R52 | 51Ω | R53 | 75Ω |
| R54 | 51r | R55 | 70Ω | R56 | 15K |
| R57 | 270Ω | R58 | 220Ω | R59 | 27K |
| R60 | 4.7K | R61 | 6.8K | R62 | 220Ω |
| R63 | 270Ω | R64 | 220Ω | R65 | 5.1K |
| R66 | 220Ω | R67 | 5.1K | R68 | 33Ω |
| R69 | 3.3K | R70 | 47Ω | R71 | 1K |
| R72 | 480Ω | R73 | 680Ω | R74 | 1.2K |
| R75 | 680Ω | R76 | 100Ω | R77 | 100Ω |
| R78 | 22K | R79 | 10K | R80 | 10K |
| R81 | 22K | R82 | 10K | R83 | 330Ω |
| R84 | 10K | R85 | 330Ω | R89 | 2K |
| C1 | 27pf | C2 | 27pf | C3 | .1uf |
| C4 | .1uf | C5 | .1uf | C6 | .1uf |
| C7 | .1uf | C8 | 100uf | C9 | .1uf |
| C10 | 1uf | C11 | 1uf | C14 | .1uf |
| C15 | .1uf | C16 | .01uf | C17 | .1uf |
| C18 | .01uf | C19 | 1uf | C20 | .01uf |
| C21 | 10uf | C22 | .1uf | C23 | 10uf |
| C24 | .01uf | C25 | .1uf | C26 | 27pf |
| C27 | 27pf | C29 | .1uf | C30 | .01uf |
| C31 | 10uf | C32 | .002uf | C33 | .0022uf |
| C34 | .1uf | C35 | 1uf | C36 | .1uf |
| C38 | 20000pf | C39 | .01uf | C40 | .01uf |
| C41 | .01uf | C42 | .1uf | C43 | .1uf |
| C44 | .1uf | C45 | .1uf | C46 | .1uf |
| C47 | .01uf | C48 | .01uf | C49 | .01uf |
| C50 | .01uf | C51 | .01uf | C52 | .01uf |
| C53 | .01uf | C54 | .1uf | C55 | .1uf |
| C56 | .1uf | C58 | .01uf | C61 | 47uf |
| C62 | .001uf | C63 | .01uf | C65 | 1uf |
| C66 | .01uf | C67 | .01uf | C68 | .01uf |
| C69 | .01uf | C70 | .01uf | C71 | 10uf |

TABLE-continued

| | | | | | |
|---|---|---|---|---|---|
| C73 | .1uf | C74 | .1uf | C75 | 27pf |
| C76 | .01uf | C77 | 180pf | C78 | 15pf |
| C79 | .1uf | C80 | .1uf | C81 | .1uf |
| C82 | 10uf | C83 | .01uf | C84 | .1uf |
| C85 | .1uf | C86 | .1uf | C87 | .1uf |
| C88 | 100pf | C89 | .1uf | C92 | 1uf |
| C93 | 1uf | C94 | 470pf | C95 | .01uf |
| C96 | 220uf | C97 | .1uf | C98 | .001uf |
| C99 | .01uf | C100 | .01uf | C101 | .1uf |
| C105 | .001uf | C106 | .001uf | C107 | .001uf |
| C110 | .1uf | | | | |
| D1-D3, D5, D7-D15 | 1N914 | | | | |
| D4 | 1N4004 | | | | |

In FIG. 9, the ultrasonic probe 14 of FIG. 1, is illustrated in an exploded longitudinal side view. The transducer body preferably includes a reduced-diameter protrusion 348 extending outwardly from its outer end with a transducer element in the end surface 349. THe diameter of the protrusion 348 is such that it may be received within, and extend into, the side wall 350 of the fluid chamber 352. Preferably, an O-ring 354 is disposed in a groove 356 extending circumferentially about the periphery of the protrusion 348 and provides a seal between the side wall 350 of the fluid chamber 352 and the protrusion 348.

In assembly of the preferred ultrasonic probe 14, the open end 358 of the flexible membrane 24 is slipped over the open outer end 360 of the fluid chamber 352 and resiliently engages the reduced-diameter portion 362 of the fluid chamber. An O-ring 364 compresses and sealingly urges the side wall portion 366 of the flexible membrane 24 into the groove 368 extending circumferentially around the reduced-diameter portion 362 of the fluid chamber. It is also possible to have the O-ring be initially attached to or be an integral part of the flexible membrane 24 for ease of assembly.

The flexible membrane 24 preferably is composed of a thin, flexible, and resilient film material which is substantially transparent to ultrasonic vibrations and is preferably substantially transparent to light passing therethrough. One such material which has been found to be acceptable is tonofilm which is a natural rubber product marketed by Clini-Tech in Littlestown, Pa. The membrane may be sterile and disposable, or non-sterile and reusable, as desired.

As is discussed below, when the flexible membrane 24 is installed on the open outer end 360 of the fluid chamber 352 and the fluid chamber is filled with water or other ultrasonic transmission fluid, the membrane's generally spherical end wall 370 bulges outwardly a predetermined distance from the transducer and surface 349. The filled flexible membrane is sufficiently resiliently deformable such that when placed against the cornea of the eye 26, as shown in FIG. 1, the end wall 370 substantially conforms to the shape of the eye's cornea. Also, if pressed against the cornea the membrane resiliently deforms before any substantial deformation of the eye occurs. Thus, the flexible membrane 24 presents a soft, resilient "cushion" which reduces the likelihood of any discomfort or irritation for the patient when the probe is placed in contact with his or her eye. Furthermore, because the flexibility of the flexible membrane 24 is such that the membrane resiliently deforms before any substantial deformation of the eye 26 occurs, very accurate measurements such as those illustrated in FIG. 1 are much easier to obtain because axial deformation and distortion of the various portions of the eye which may result from compression of the eye are avoided.

FIG. 9 also illustrates a valve apparatus for introducing water or other ultrasonic transmission fluid into the interior of the fluid chamber 352 and the flexible membrane 24. The protrusion 348 on the transducer body 347 includes a recessed portion 374 at its outer end. Because of the sealing engagement between the fluid chamber 352 and the protrusion 348 provided by the O-ring 354, the fluid chamber 352 may be mounted in a freely rotatable relationship on the protrusion 348. Thus, the fluid chamber 352 may be rotated to a position where a filling aperture 376 extending through the side wall 350 is aligned with the recessed portion 374 on the protrusion 348. Such alignment provides a fluid communication between the exterior and the interior of the fluid chamber by way of the filling aperture 376 and the recessed portion 374. Once the fluid chamber 352 and the flexible membrane 24 are filled with water or another suitable ultrasonic transmission fluid, any resultant air bubbles are removed, such as by tapping the fluid chamber against a hard surface. The fluid chamber 352 is then again rotated so that the filling aperture 376 is no longer aligned with the recessed portion 374, thereby blocking the above-mentioned fluid communication between the exterior and the interior of the fluid chamber so that the fluid will not leak therefrom.

In order to achieve the proper performance and desired degree of resilient deformation of the filled flexible membrane 24, the membrane must be mounted on the reduced-diameter portion 362 of the fluid chamber such that the end wall 370 of the flexible membrane bulges outwardly a predetermined distance from the transducer end surface 349. An acceptable predetermined distance has been found to be in the range of 28 mm to 32 mm for a flexible membrane having a side wall thickness of 0.1 mm±0.02 mm. In order to assist the operator of the ultrasound system in properly installing the flexible membrane 24 such that its end wall 370 bulges outwardly from the fluid chamber by such predetermined distance, a gauge apparatus such as that illustrated by the exemplary assembly gauge 378 in FIG. 10 may be provided.

The assembly gauge 378 includes a base 380 and a gauge post 382. In order to properly mount the flexible membrane 24, the fluid chamber 352 is slipped over the gauge post 382 against the base 380 such that the gauge post protrudes outwardly from the open end 360 of the fluid chamber. The open end 358 of the flexible membrane 24 is then slipped over and into resilient engagement with the reduced-diameter portion 362 of the fluid chamber until the end wall 370 contacts the outer end of the gauge post 382. The O-ring 364 is then installed to resiliently and compressingly trap the side wall 366 of the flexible membrane between the O-ring 364 and the groove 368 on the reduced-diameter portion 362. Thus, when the fluid chamber 352, with the flexible membrane 24 installed thereon, is removed from the gauge post 381 and installed as described above on the transducer 347, and the fluid chamber 30 and the flexible membrane 24 are filled with ultrasonic transmissive fluid, the end wall 370 of the flexible membrane protrudes or bulges outwardly from the surface 349 of the transducer by the desired predetermined distance.

A partial view in cross-section of an ultrasonic probe 14, with an alternate retention apparatus for the flexible membrane 24, is illustrated in FIG. 11. If desired or found necessary to retain the flexible membrane 24 on the fluid chamber 352 more securely in order to insure against leakage of the ultrasonic transmission fluid, the ultrasonic probe 14 may be equipped with an alternate retention sleeve 354, which slidably surrounds the reduced-diameter portion 362 of the fluid chamber 352. The retention sleeve 384 is retracted in an inward direction until the flexible membrane is installed with its side wall 366 resiliently engaging the reduced-diameter portion 362, and the O-ring 364 is installed thereon as described above. The retention sleeve 384 may then be slidably urged in an outward direction to circumscribe and compressingly engage the side wall 366 of the flexible membrane 24 and the O-ring 364 to more positively and securely anchor and seal the flexible membrane 24 to the fluid chamber 352.

While it will be apparent that the preferred embodiment of the present invention is well calculated to provide the features and advantages above stated, it will be appreciated that the invention is susceptible to modification, variation and change without departing from the proper scope or fair meaning of the subjoined claims.

We claim:

1. An ultrasonic diagnostic scanner for measuring at least one parameter of an eye, comprising:
    transmitter means for causing a transducer to transmit an ultrasonic signal;
    receiver means for receiving echo signals representing reflections of said transmitted ultrasonic signal and for producing a peak signal only at substantially the maximum amplitude of said echo signals when said echo signals exceed a predetermined threshold level which is below said maximum amplitude;
    programmable means responsive to said peak signals for producing a first count signal indicative of the time between the transmission of said ultrasonic signal and the occurrence of a selectable number of peak signals and for producing a second count signal indicative of the time between the occurrence of predetermined peak signals;
    microcomputer means for controlling said transmitter means and said programmable means, said microcomputer means determining said selectable number and said predetermined peak signals, and for determining said eye parameter from at least one of count signals; and
    output means responsive to said microcomputer means for generating a perceptible output indicative of said eye parameter.

2. The ultrasonic diagnostic scanner according to claim 1, wherein said eye parameter is the axial length of said eye, and at least two of said peak signals represent predetermined tissue boundaries used to determine the axial length of said eye.

3. The ultrasonic diagnostic scanner according to claim 2, wherein said programmable means includes first counter means for producing a count signal in response to a predetermined clock rate, second counter means for counting the number of peak signals produced by said receiver means, control logic means for generating a strobe signal which operates to initiate said first counter means in response to the first peak signal produced by said receiver means, and digital comparator means comparing the number of peak signals counted by said second counter means with a selected peak signal number produced by said microcomputer means and for producing a halt signal which operates to disable said first counter means.

4. The ultrasonic diagnostic scanner according to claim 3, wherein said receiver means also generates an edge signal whenever said echo signals exceed said predeterminable threshold level, and said programmable means also produces count signals indicative of the time between the transmission of said ultrasonic signal and the occurrence of a selected number of edge signals.

5. The ultrasonic diagnostic scanner according to claim 4, wherein said control logic means of said programmable means causes said second counter means to count the number of edge signals produced by said receiver means instead of the number of peak signals in response to an edge command signal from said microcomputer means, and said digital comparator means thereby compares the number of edge signals counted by said second counting means with a selected edge signal number produced by said microcomputer means.

6. The ultrasonic diagnostic scanner according to claim 4, further including threshold level adjustment means for adjusting said predeterminable threshold level in response to a threshold level command signal from said microcomputer means.

7. The ultrasonic diagnostic scanner according to claim 4, wherein said output means includes liquid crystal display means for visually displaying an echo histogram of said echo signals.

8. The ultrasonic diagnostic scanner according to claim 1, further including sensitivity adjustment means for maintaining a predetermined amplitude level of at least one of said echo signals in response to an automatic gain control command signal from said microcomputer means.

9. The ultrasonic diagnostic scanner according to claim 8, wherein said receiver means includes at least one amplifier stage, and said sensitivity adjustment means controls the gain of said receiver means amplifier stage.

10. The ultrasonic diagnostic scanner according to claim 1, wherein said microcomputer means includes means for determining a corneal depression condition in response to a predetermined change in the time between the transmission of said ultrasonic signal and the occurrence of a predetermined peak signal, and said output means includes means for generating a perceptible output indicative of said corneal depression condition.

11. The ultrasonic diagnostic scanner according to claim 1, wherein said microcomputer means includes means for determining an axial misalignment condition.

12. The ultrasonic diagnostic scanner according to claim 11, wherein said axial misalignment determining means is responsive to a predetermined time difference between the occurrence of two selected peak signals.

13. A method of measuring the axial length of an eye, comprising the steps of:
    (a) transmitting an ultrasonic signal;
    (b) receiving echo signals representing reflections of said transmitted ultrasonic signal;
    (c) producing a peak signal at substantially the maximum amplitude of said echo signals when said echo signals exceed a predeterminable threshold level;
    (d) producing a count signal indicative of the time between the transmission of said ultrasonic signal and the occurrence of a selected number of said peak signals;
    (e) storing said count signal;
    (f) repeating steps (a) through (e) for a first predetermined number of times at a predetermined rate and producing a first average signal from said stored count signals;
(g) storing said first average signal;
(h) repeating steps (a) through (g) for a second predetermined number of times and producing a second average signal from said first average signals;
(i) determining said eye parameter from said second average signal; and
(j) generating a perceptible output indicative of said eye parameter.

14. The method according to claim 13, further including the step of determining if said count signal is within a predetermined range, and repeating steps (a) through (d) until said count signal is within said predetermined range.

15. A method of detecting an axial misalignment condition during a measurement of the axial length of an eye with an ultrasonic diagnostic scanner having transmitter means for causing a transducer to transmit an ultrasonic signal, and receiver means for receiving echo reflections of said transmitted ultrasonic signal and for producing echo signals indicative of predetermined tissue boundaries of said eye, comprising the steps of:
(a) measuring the time between a first predetermined echo signal and a second predetermined echo signal;
(b) determining if the time between said first and second predetermined echo signals is within a predetermined range indicative of an axial alignment condition; and
(c) preventing an inaccurate axial length indicative output from said ultrasonic diagnostic scanner if the time between said first and second predetermined echo signals is outside of said predetermined range.

16. The method according to claim 15, wherein said measuring step is repeated until the time between said first and second predetermined echo signals is within said predetermined range.

17. The method according to claim 16, wherein the time between said first predetermined echo signal and a plurality of other predetermined echo signals are individually measured, and each of said measuring steps is repeated until the time differences between said first predetermined echo signal and said other predetermined echo signals are within a corresponding plurality of predetermined ranges.

18. A method of detecting a corneal depression condition during a measurement of the axial length of an eye with an ultrasonic diagnostic scanner having transmitter means for causing a transducer to transmit an ultrasonic signal, receiver means for receiving echo reflections of said transmitted ultrasonic signal and for producing echo signals indicative of predetermined tissue boundaries of said eye, and a probe having a membrane, comprising the steps of:
(a) initializing said scanner prior to measuring said axial length of the eye by measuring the time between the transmission of said ultrasonic signal and an echo signal indicative of said membrane defining a predetermined time representing the absence of said corneal depression condition;
(b) measuring the time between the transmission of said ultrasonic signal and a predetermined echo signal after said scanner has been initialized;
(c) determining said corneal depression condition from a predetermined correlation between said time measured in step (b) and said predetermined time representing the absence of said corneal depression condition; and
(d) generating a perceptible output indicative of said corneal depression condition.

19. The method according to claim 18, wherein said predetermined echo signal represents the cornea of said eye.

20. A method of displaying an echo histogram in an ultrasonic diagnostic scanner for measuring the axial length of an eye, having transmitter means for causing a transducer to transmit an ultrasonic signal, receiver means for receiving echo signals representing reflections of said transmitted ultrasonic signal and for producing an edge signal whenever said echo signals exceed a predeterminable threshold level, threshold level adjustment means for adjusting and predeterminable threshold level, means for measuring the time between the transmission of said ultrasonic signal and the occurrence of said edge signals, memory means for storing data and digital display means for displaying said histogram, comprising the steps of:
(a) transmitting said ultrasonic signal,
(b) detecting the occurrence of each of said edge signals at initial predetermined threshold level;
(c) storing a map of the occurrence of said edge signals in specific memory locations determined by said programmable means;
(d) incrementing said threshold level to the next predetermined threshold level;
(e) repeating steps (a) through (d) until said threshold level has been incremented a predeterminable number of threshold levels; and
(f) enabling said digital display means to display said histogram in accordance with the values stored in said specific memory locations.

21. An ultrasonic diagnostic scanner for measuring the axial length of an eye, comprising:
transmitter means for causing a transducer to transmit an ultrasonic signal;
receiver means for receiving echo signals representing reflections of said transmitted ultrasonic signal and for producing a peak signal at substantially the maximum amplitude of said echo signals when said echo signals exceed a predeterminable threshold level, at least two of said peak signals representing predetermined tissue boundaries used to determine the axial length of said eye;
programmable means responsive to said peak signals for producing count signals indicative of the times between the transmission of said ultrasonic signal and the occurrence of a selected number of peak signals and between the occurrence of predetermined peak signals;
microcomputer means for controlling said transmitter means and said programmable means, and for determining said eye parameter from at least one of count signals;
said programmable means including first counter means for producing a count signal in response to a predetermined clock rate, second counter means for counting the number of peak signals produced by said receiver means, control logic means for generating a strobe signal which operates to initiate said first counter means in response to the first peak signal produced by said receiver means, and digital comparator means comparing the number of peak signals counted by said second counter means with a selected peak signal number produced by said microcomputer means for producing a halt signal which operates to disable said first counter means; and output means responsive to said microcomputer means for generating a perceptible output indicative of said eye parameter.

22. An ultrasonic diagnostic scanner for measuring at least one parameter of an eye, comprising:

transmitter means for causing a transducer to transmit an ultrasonic signal;

receiver means for receiving echo signals representing reflections of said transmitted ultrasonic signal;

differentiator and comparator means for producing a peak signal only at substantially the maximum amplitude of said echo signals when said echo signals exceed a predeterminable threshold level which is below said maximum amplitude, said differentiator and comparator means including a differentiator circuit producing a signal that is proportional to the slope of said echo signals in order for the maximum amplitude of said echo signals to be located;

means responsive for producing a count signal which is responsive to the occurrence of at least one peak signal;

microcomputer means for determining said eye parameter from said count signal; and output means responsive to said microcomputer means for generating a perceptible output indicative of said eye parameter.

23. The ultrasonic diagnostic scanner according to claim 22, wherein said eye parameter is the thickness of the cornea.

24. The diagnostic scanner according to claim 22, where said differentiator circuit produces a signal having a substantially zero voltage level when a received echo signal changes from a positive to a negative slope, and said differentiator and comparator means further including a zero crossover circuit which detects a zero level signal, a comparator circuit which is responsive to said predetermined pressure level and a received echo signal, and logic circuit means for producing said peak signal in response to the output from said comparator circuit and said zero crossover circuit.

* * * * *

UNITED STATES PATENT AND TRADEMARK OFFICE
CERTIFICATE OF CORRECTION

PATENT NO. : 4,564,018

DATED : January 14, 1986

INVENTOR(S) : Hutchison, et al.

It is certified that error appears in the above-identified patent and that said Letters Patent is hereby corrected as shown below:

| | | |
|---|---|---|
| Column 4, | line 13 | "tranducer" should be --transducer-- |
| Column 4, | line 42 | "FIg." should be --Fig.-- |
| Column 5, | line 52 | "sclear" should be --sclera-- |
| Column 8, | line 37 | "numeral" should be --numerical-- |
| Column 10, | line 15 | "masurements" should be --measurements-- |
| Column 10, | line 56 | "desplayed" should be --displayed-- |
| Column 11, | line 43 | "at" should be --to-- |
| Column 11, | line 56 | "timer/circuit" should be --timer/counter-- |
| Column 12, | line 55 | "substantialy" should be --substantially-- |
| Column 14, | lines 12,13 | "logrithmic" should be --logarithmic-- |
| Column 16, | line 44 | "time/counter" should be --timer/counter-- |
| Column 18, | line 37 of the table | "51r" should be "51$\Omega$" |

UNITED STATES PATENT AND TRADEMARK OFFICE
CERTIFICATE OF CORRECTION

PATENT NO. : 4,564,018

DATED : January 14, 1986

INVENTOR(S) : Hutchison, et al.

It is certified that error appears in the above-identified patent and that said Letters Patent is hereby corrected as shown below:

| | | |
|---|---|---|
| Column 18, | line 43 of the table | "480Ω" should be "680Ω" |
| Column 19, | line 19 | "THe" should be --The-- |
| Column 19, | line 28 | "and" should be --end-- |
| Column 20, | line 31 | "predetermined" should be --predeterminable-- |
| Column 20, | line 59 | "381" should be --382-- |
| Column 20, | line 61 | "transmissive" should be --transmission-- |
| Column 24, | line 16 | "and" should be --said-- |

Signed and Sealed this

Eighteenth Day of November, 1986

*Attest:*

DONALD J. QUIGG

*Attesting Officer*     *Commissioner of Patents and Trademarks*